US008252593B2

(12) United States Patent
Fukuma et al.

(10) Patent No.: US 8,252,593 B2
(45) Date of Patent: Aug. 28, 2012

(54) SAMPLE ANALYZER AND CALIBRATION METHOD OF SAMPLE ANALYZER

(75) Inventors: Daigo Fukuma, Kobe (JP); Masaharu Shibata, Kobe (JP)

(73) Assignee: Sysmex Corporation, Kobe (JP)

( * ) Notice: Subject to any disclaimer, the term of this patent is extended or adjusted under 35 U.S.C. 154(b) by 215 days.

(21) Appl. No.: 12/589,863

(22) Filed: Oct. 28, 2009

(65) Prior Publication Data

US 2010/0105142 A1   Apr. 29, 2010

(30) Foreign Application Priority Data

Oct. 28, 2008   (JP) .................................. 2008-277437

(51) Int. Cl.
*G01N 31/00* (2006.01)
*G01N 33/00* (2006.01)

(52) U.S. Cl. ................... 436/8; 436/43; 436/47; 422/65; 422/68.1; 73/1.01; 73/1.02

(58) Field of Classification Search ................ 436/8, 43, 436/47, 50, 55; 422/63, 65, 67, 68.1; 73/1.01, 73/1.02
See application file for complete search history.

(56) References Cited

U.S. PATENT DOCUMENTS

| 2008/0240988 | A1* | 10/2008 | Wakamiya et al. | .......... 422/68.1 |
| 2010/0248293 | A1* | 9/2010 | Kuwano et al. | .................. 435/29 |
| 2010/0282003 | A1* | 11/2010 | Hamada et al. | ............ 73/863.91 |
| 2010/0332144 | A1* | 12/2010 | Nagai et al. | ..................... 702/19 |

FOREIGN PATENT DOCUMENTS

JP            06-308131          11/1994

* cited by examiner

*Primary Examiner* — Maureen Wallenhorst
(74) *Attorney, Agent, or Firm* — Brinks Hofer Gilson & Lione

(57) ABSTRACT

A sample analyzer is disclosed that includes a first measurement unit for measuring a sample, a second measurement unit for measuring a sample, and an information processing unit for acquiring a first analysis result based on a result of the measurement by the first measurement unit and a second analysis result based on a result of the measurement by the second measurement unit. The information processing unit is configured to correct the first analysis result based on a first correction value, correct the second analysis result based on a second correction value, update the first correction value, and update the second correction value. A calibration method of a sample analyzer is also disclosed.

20 Claims, 19 Drawing Sheets

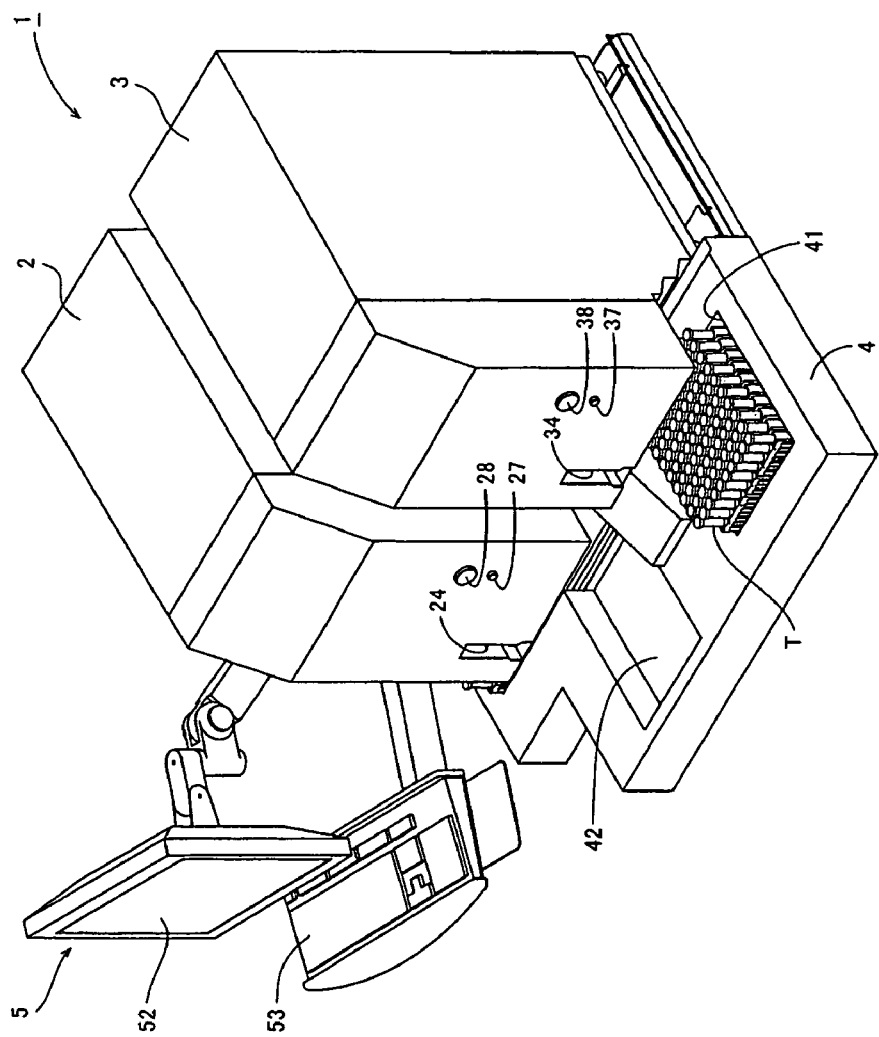

FIG. 19

AUTOMATIC SERVICE CALIBRATION M116M^11001

TARGET SETTING... ~B1

| Sample No. | Date | Time | Parameter Inst.ID | WBC_CAL WBC | RBC_CAL RBC | HGB_CAL HGB | PLT_CAL PLT | ... |
|---|---|---|---|---|---|---|---|---|
| 1 | 2008/8/5 | 10:11:00 | M116M^11001 | 42 | 430 | 129 | 23 | ... |
| 2 | 2008/8/5 | 10:12:00 | M116M^11001 | 43 | 432 | 129 | 22 | ... |
| 3 | 2008/8/5 | 10:13:00 | M116M^11001 | 44 | 430 | 130 | 24 | ... |
| 4 | 2008/8/5 | 10:14:00 | M116M^11001 | 42 | 436 | 131 | 21 | ... |
| 5 | 2008/8/5 | 10:15:00 | M116M^11001 | 41 | 441 | 129 | 22 | ... |
| 6 | 2008/8/5 | 10:16:00 | M116M^11001 | 44 | 432 | 130 | 23 | ... |
| 7 | 2008/8/5 | 10:17:00 | M116M^11001 | 42 | 432 | 130 | 25 | ... |
| 8 | 2008/8/5 | 10:18:00 | M116M^11001 | 41 | 429 | 128 | 22 | ... |
| 9 | 2008/8/5 | 10:19:00 | M116M^11001 | 43 | 428 | 129 | 20 | ... |
| 10 | 2008/8/5 | 10:20:00 | M116M^11001 | 42 | 434 | 129 | 23 | ... |
| | | | Average | 42 | 432 | 129 | 22 | ... |
| | | | Target | 43 | 433 | 130 | 23 | ... |
| | | | Current Cal. | 1000 | 1000 | 1000 | 1000 | ... |
| | | | New Cal. | 1023 | 1002 | 1007 | 1045 | ... |

A1, A2, A3, A4, A5

B2 ~ OK
B3 ~ CANCEL
B4

SAMPLE ANALYZER AND CALIBRATION METHOD OF SAMPLE ANALYZER

RELATED APPLICATIONS

This application claims priority under 35 U.S.C. §119 to Japanese Patent Application No. 2008-277437 filed Oct. 28, 2008, the entire content of which is hereby incorporated by reference.

BACKGROUND OF THE INVENTION

1. Field of the Invention

The present invention relates to a sample analyzer, and a calibration method of the sample analyzer.

2. Description of the Related Art

Various sample analyzers such as multi-item blood cell analyzer, blood coagulation measurement apparatus, immune analyzer, biochemical analyzer, and urine analyzer are conventionally known. In such sample analyzers, calibration of the apparatus is performed on a regular basis. In the calibration of the apparatus, the measurement of the same sample is executed plural times to check that the variation in the analysis result is within a predetermined range prior to the measurement of the sample for calibration.

Japanese Laid-Open Patent Publication No. 6-308131 describes a data processing device connected to a plurality of automatic analyzers. The data processing device of Japanese Laid-Open Patent Publication No. 6-308131 tabulates the measurement result of the sample for calibration in each automatic analyzer, and automatically performs calculation, and correction of weigh-in coefficient.

However, in the data processing device described in Japanese Laid-Open Patent Publication No. 6-308131, the same sample for calibration needs to be measured in each of the plurality of automatic analyzers. If a "calibrator" (sample, which concentration of component to be measured is known, and sample prepared to use mostly for the calibration of the analyzer) is used for the sample for calibration, the cost becomes high as the calibrator is very expensive. When calibrating one automatic analyzer of the plurality of automatic analyzers, then measuring a sample irrelevant to calibration of the one automatic analyzer in each automatic analyzer as a sample for calibration, and performing a correlation process on the one calibrated automatic analyzer, the sample needs to be measured in all automatic analyzers, and waste of the sample may arise.

SUMMARY OF THE INVENTION

The scope of the present invention is defined solely by the appended claims, and is not affected to any degree by the statements within this summary.

A first sample analyzer embodying features of the present invention includes: a first measurement unit for measuring a sample; a second measurement unit for measuring a sample; and an information processing unit for acquiring a first analysis result based on a result of the measurement by the first measurement unit and a second analysis result based on a result of the measurement by the second measurement unit; wherein the information processing unit is configured to: correct the first analysis result based on a first correction value, correct the second analysis result based on a second correction value, update the first correction value, and update the second correction value, wherein the information processing unit is further configured to: update the first correction value based on an analysis result obtained through a measurement of a sample for calibration by the first measurement unit, and update the second correction value based on a plurality of analysis results obtained by measuring same sample over plural times by the second measurement unit, and a corrected analysis result, and wherein the corrected analysis result is obtained by correcting, an analysis result obtained by measuring the same sample by the first measurement unit, by using the first correction value updated by the information processing unit.

A first calibration method of a sample analyzer comprising a first measurement unit and a second measurement unit embodying features of the present invention includes steps of: analyzing step of acquiring an analysis result based on a result of the measurement by the first and the second measurement units; first correcting step of correcting an analysis result based on the measurement of the sample by the first measurement unit based on a first correction value; second correcting step of correcting an analysis result based on the measurement of the sample by the second measurement unit based on a second correction value; first calibration step of updating the first correction value using the analysis result obtained when the first sample measurement unit measures a sample for calibration; and second calibration step of updating the second correction value using a plurality of analysis results obtained by measuring a same sample over plural times by the second sample measurement unit, and a corrected analysis result corrected by the first correction value in which the analysis result based on the measurement by the first measurement unit of the same sample is updated.

A second calibration method of a sample analyzer comprising a first measurement unit and a second measurement unit embodying features of the present invention includes steps of: measuring a sample for calibration by the first measurement unit and calibrating the first measurement unit; measuring same sample for reproducibility check by the second measurement unit over plural times; determining whether or not variation in a plurality of analysis results obtained by measuring the same sample for reproducibility check over plural times is within a predetermined range; measuring the sample for reproducibility check by the calibrated first measurement unit and acquiring an analysis result of the sample for reproducibility check; and calibrating the second measurement unit based on the analysis result of the sample for reproducibility check by the first measurement unit and the analysis result of the sample for reproducibility check by the second measurement unit.

BRIEF DESCRIPTION OF THE DRAWINGS

FIG. 1A is a perspective views showing an overall configuration of a sample analyzer according to an embodiment;

FIG. 19 is a view showing one example of the manual calibration screen; and

DETAILED DESCRIPTION OF THE PREFERRED EMBODIMENTS

A preferred embodiment of the present invention will be described below with reference to the drawings.

The present embodiment relate to a sample analyzer, including two measurement units of a first measurement unit and a second measurement unit, and an information processing unit communicably connected to the first measurement unit and the second measurement unit, for performing calibration of the second measurement unit using a sample for reproducibility check used in the calibration of the first measurement unit.

[Configuration of Sample Analyzer]

Figure 1B:
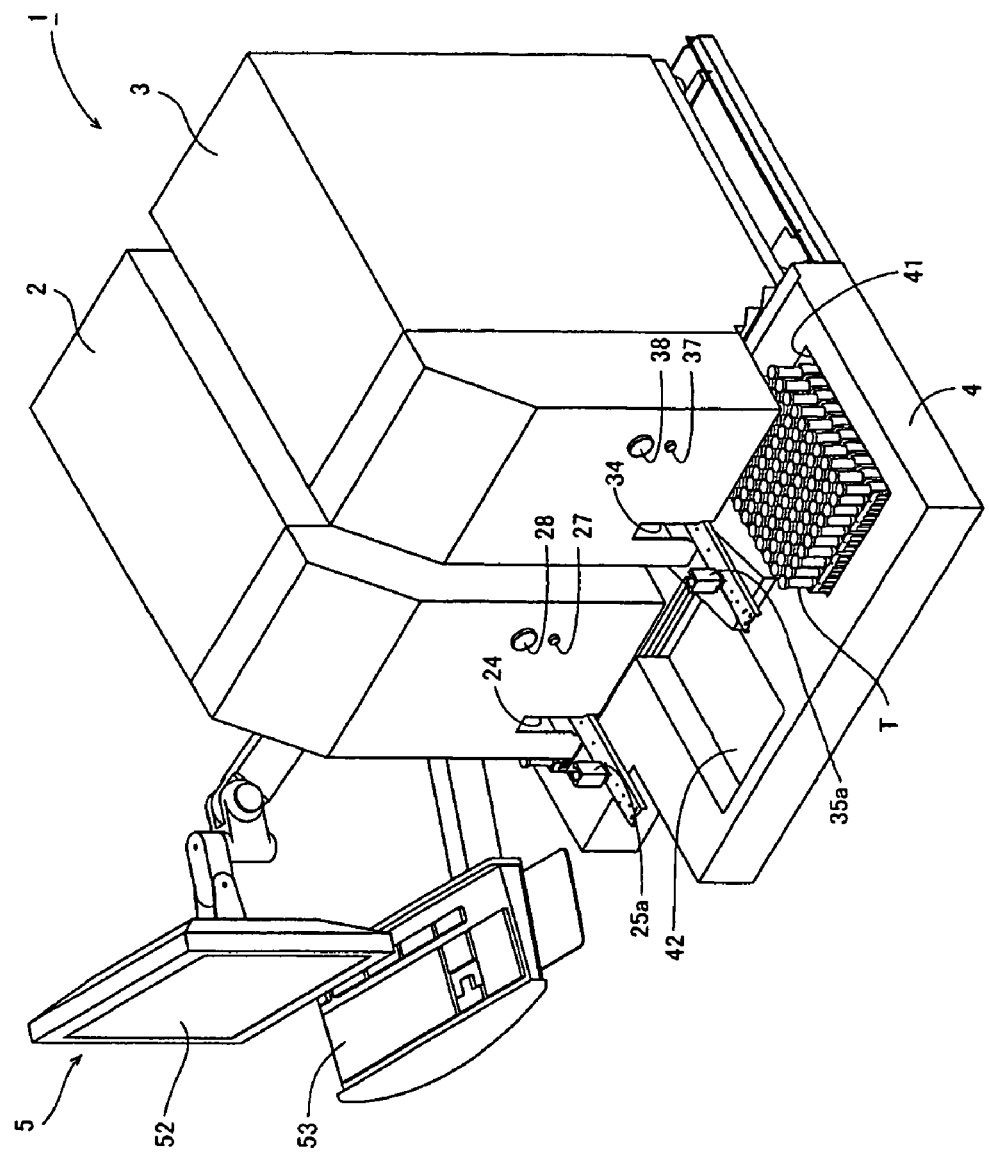
FIG. 1B is a perspective views showing an overall configuration of the sample analyzer according to the embodiment.

FIGS. 1A and 1B are perspective views showing an overall configuration of the sample analyzer according to the present embodiment. The sample analyzer 1 according to the present embodiment is a multi-item blood cell analyzer for detecting the white blood cells, the red blood cells, the platelets, and the like contained in the blood sample, and counting each blood cells. As shown in FIGS. 1A and 1B, the sample analyzer 1 includes a first measurement unit 2, a second measurement unit 3, a sample conveyance unit 4 arranged on the front surface side of the first measurement unit 2 and the second measurement unit 3, and an information processing unit 5 capable of controlling the first measurement unit 2, the second measurement unit 3, and the sample conveyance unit 4.

Figure 2:
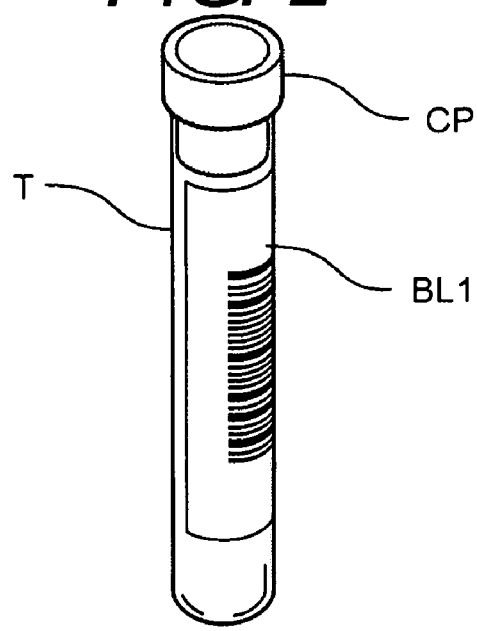
FIG. 2 is a perspective view showing an outer appearance of a sample container.
Figure 3:
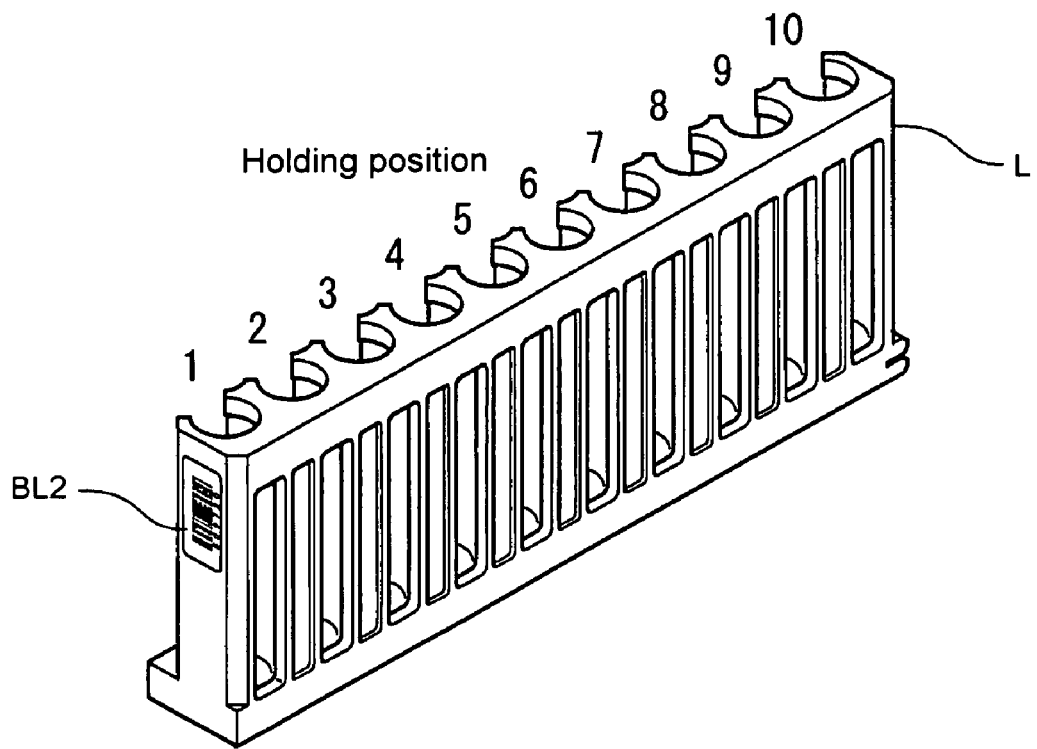
FIG. 3 is a perspective view showing an outer appearance of a sample rack.

FIG. 2 is a perspective view showing an outer appearance of a sample container accommodating a sample, and FIG. 3 is a perspective view showing an outer appearance of a sample rack for holding a plurality of sample containers. As shown in FIG. 2, the sample container T has a tubular shape, and the upper end thereof is opened. The blood sample collected from a patient is accommodated therein, and the opening at the upper end is sealed by a lid CP. The sample container T is made of a glass or a synthetic resin having translucency, so that the blood sample inside can be seen. A barcode label BL1 is attached to the side surface of the sample container T. A barcode indicating a sample ID is printed on the barcode label BL1. As shown in FIG. 3, the sample rack L can hold ten sample containers T side by side. Each sample container T is held in a perpendicular state (standing state) in the sample rack L. A barcode label BL2 is attached to the side surface of the sample rack L. A barcode indicating a rack ID is printed on the barcode label BL2.

<Configuration of Measurement Unit>

Figure 4:
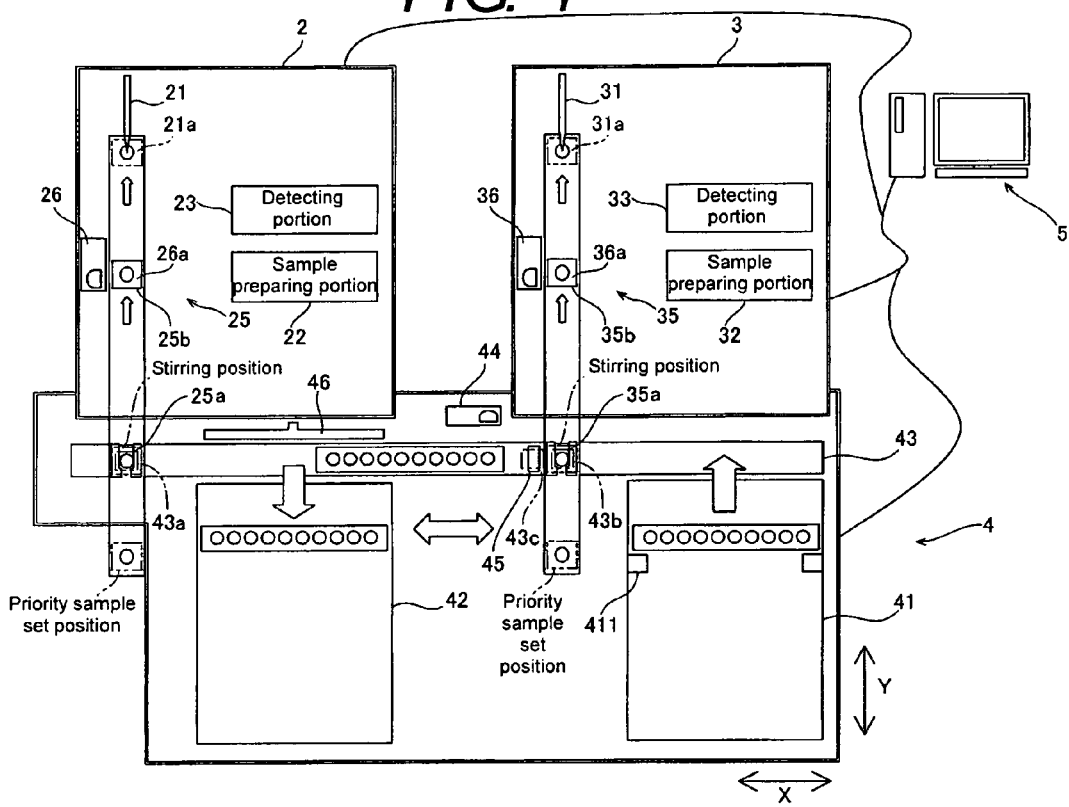
FIG. 4 is a block diagram showing a configuration of a measurement unit according to the embodiment.

FIG. 4 is a block diagram showing a configuration of the measurement unit. As shown in FIG. 4, the first measurement unit 2 includes a sample aspirating portion 21 for aspirating the blood or the sample from the sample container (blood collecting tube) T, a sample preparing portion 22 for preparing a measurement sample used in the measurement from the blood aspirated by the sample aspirating portion 21, and a detecting portion 23 for detecting the blood cell from the measurement sample prepared by the sample preparing portion 22. The first measurement unit 2 further includes a take-in port 24 (see FIGS. 1A and 1B) for taking in the sample container T accommodated in the sample rack L conveyed by the rack conveyance portion 43 of the sample conveyance unit 4 into the first measurement unit 2, and a sample container conveyance portion 25 for taking in the sample container T from the sample rack L into the first measurement unit 2 and conveying the sample container T to the aspirating position by the sample aspirating portion 21. As shown in FIGS. 1A and 1B, sample setting portion open/close buttons 27, 37 and priority sample measurement start buttons 28, 38 are provided on the outer side surface of the first measurement unit 2 and the second measurement unit 3 respectively.

As shown in FIG. 4, an aspirating tube (not shown) is arranged at the distal end of the sample aspirating portion 21. The sample aspirating portion 21 is movable in the vertical direction, and is moved to the lower side so that the aspirating tube passes through the lid CP of the sample container T conveyed to the aspirating position to aspirate the blood inside.

The sample preparing portion 22 includes a plurality of reaction chambers (not shown). The sample preparing portion 22 is connected to a reagent container (not shown), and can supply the reagent such as a stain reagent, a hemolyzing agent, and a diluted solution to the reaction chamber. The sample preparing portion 22 is also connected to the aspirating tube of the sample aspirating portion 21, and can supply the blood sample aspirated by the aspirating tube to the reaction chamber. Such sample preparing portion 22 mixes and stirs the sample and the reagent in the reaction chamber, and prepares the sample for measurement (measurement sample) by the detecting portion 23.

The detecting portion 23 can perform the RBC (Red Blood Cell) detection and the PLT (Platelet) detection through the sheath flow DC detection method. In the detection of the RBC and the PLT by the sheath flow DC detection method, the measurement of the measurement sample, in which the sample and the diluted solution are mixed, is performed, wherein the information processing unit 5 performs the analyzing process on the obtained measurement data to measure the RBC and the PLT. The detecting portion 23 can perform the HGB (Hemoglobin) detection through the SLS-hemoglobin method, and is configured to perform the detection of WBC (White Blood Cell), NEUT (Neutrophil Cell), LYMPH (Lymph Cell), EO (Eosinophil), BASO (Basophil) and MONO (Monocyte) through the flow cytometry method using the semiconductor laser. In the detecting portion 23, detecting methods differ for the detection of the WBC not involving the detection of five classification of the white blood cell, that is, the NEUT, the LYMPH, the EO, the BASO and the MONO, and for the detection of the WBC involving five classification of the white blood cell. In the detection of the WBC not involving five classification of the white blood cell, the measurement of the measurement sample, in which the sample, the hemolyzing agent and the diluted solution are mixed, is performed, wherein the information processing unit 5 performs the analyzing process on the obtained measurement data to measure the WBC. On the other hand, in the detection of the WBC involving five classification of the white blood cell, the measurement of the measurement sample, in which the stain reagent, the hemolyzing agent and the diluted solution are mixed, is performed, wherein the information processing unit 5 performs the analyzing process on the obtained measurement data to measure the NEUT, the LYMPH, the EO, the BASO, the MONO and the WBC.

Figure 5:
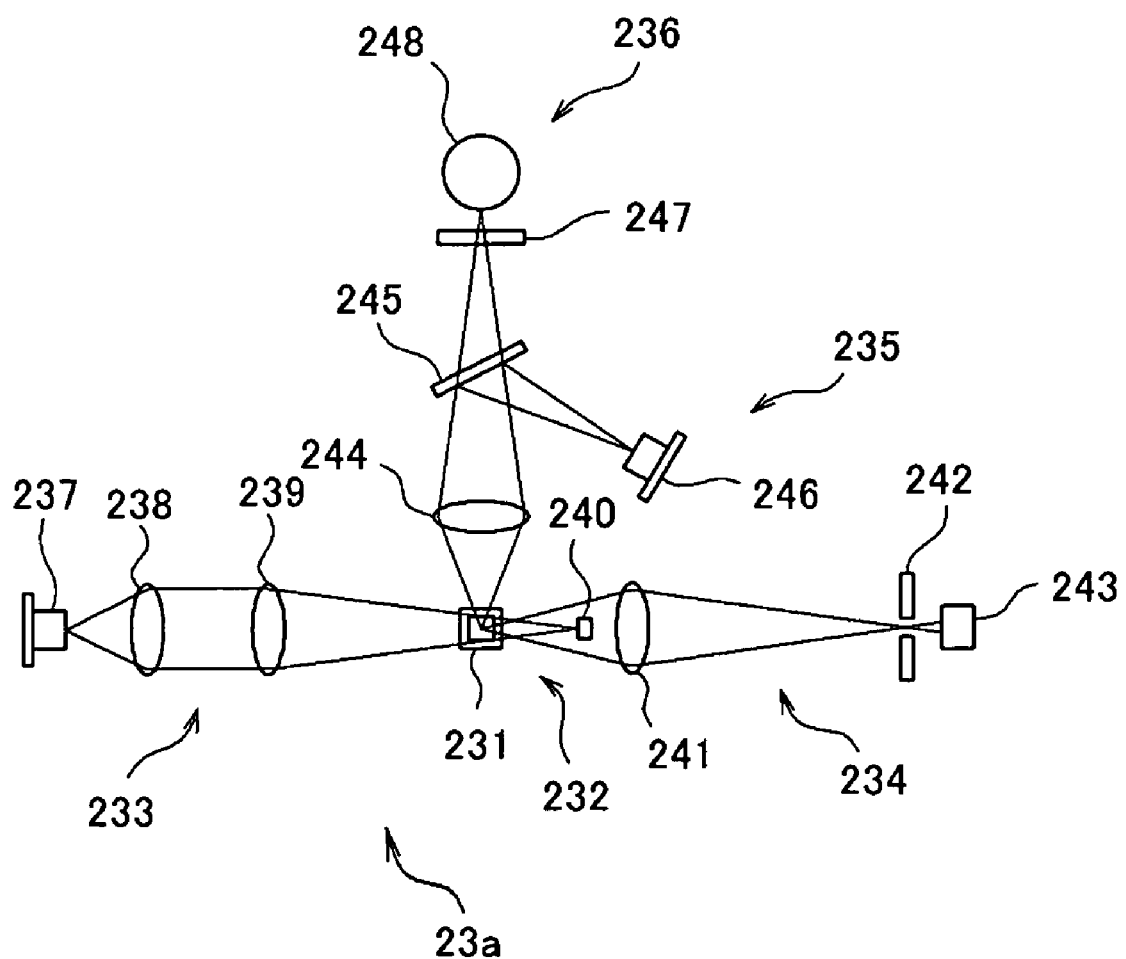
FIG. 5 is a schematic view showing an outline configuration of an optical detecting portion for WBC/DIFF (five classification of white blood cell) detection.

FIG. 5 shows an outline configuration of an optical detecting portion for detecting the WBC/DIFF (five classification of white blood cell) arranged in the detecting portion 23. The optical detecting portion 23a sends the measurement sample to a flow cell 231, generates a liquid flow in the flow cell 231, and irradiates a semiconductor laser light on the blood cell contained in the liquid flow passing through the flow cell 231 for measurement, and includes a sheath flow system 232, a beam spot formation system 233, a forward scattered light receiving system 234, a lateral scattered light receiving system 235, and a lateral fluorescent light receiving system 236.

In the sheath flow system 232, the samples flow through the flow cell 231 while being covered with sheath liquid and the blood cells lined in a line to enhance the accuracy degree of the blood cell counting and the reproducibility. The beam spot system 233 is configured such that the light irradiated from a semiconductor laser 237 is irradiated on the flow cell 231 through a collimator lens 238 and a capacitor lens 239. The beam post system 233 also includes a beam stopper 240.

The forward scattered light receiving system 234 collects the scattered light to the forward side by a forward light collecting lens 241, and receives the light passed through a pin hole 242 by a photodiode (forward scattered light receiving portion) 243.

The lateral scattered light receiving system 235 collects the scattered light to the side by a lateral light collecting lens 244, reflects some light with a dichroic mirror 245, and receives the light by a photodiode (lateral scattered light receiving portion) 246.

The light scattering is a phenomenon that occurs when a particle such as blood exists in the advancing direction of the light as an obstruction so that the light changes its advancing direction. Information related to size and material of the particle can be obtained by detecting the scattered light. In particular, information related to the size of the particle (blood cell) can be obtained from the forward scattered light. Information of the interior of the particle can be obtained from the lateral scattered light. When laser light is irradiated on the blood cell particle, the lateral scattered light intensity depends on the complexity of the interior of the cell (shape of core, size, density, amount of granulated powder). Therefore, the measurement of the classification of white blood cell, and other measurements can be performed using such characteristic of the lateral scattered light intensity.

The lateral fluorescent light receiving system 236 is configured such that the light transmitted through the dichroic mirror 245 further passes a spectral filter 247, and is received by a photomultiplier (fluorescent light receiving portion) 248.

When light is irradiated on a fluorescent substance such as stained blood, the light of wavelength longer than the wavelength of the irradiated light is emitted. The intensity of the fluorescence becomes stronger if well stained, and information on the staining degree of the blood cell can be obtained by measuring the fluorescence intensity. Therefore, the measurement of the classification of white blood cell and other measurements can be performed by the difference in the (lateral) fluorescence intensity.

Returning to FIG. 4, the configuration of the sample container conveyance portion 25 will be described. The sample container conveyance portion 25 includes a hand portion 25a capable of gripping the sample container T. The hand portion 25a includes a pair of gripping members arranged facing each other, and can approach or separate the gripping members to and from each other. The sample container T can be gripped by approaching the relevant gripping members with the sample container T in between. The sample container conveyance portion 25 can move the hand portion 25a in the up and down direction and in the front and back direction (Y direction), and can oscillate the hand portion 25a. Thus, the sample container T accommodated in the sample rack L and positioned at the first sample supply position 43a can be gripped by the hand portion 25a, and the sample container T can be taken out from the sample rack L by moving the hand portion 25a upward in the relevant state, and the sample in the sample container T can be stirred by oscillating the hand portion 25a.

The sample container conveyance portion 25 includes a sample container setting portion 25b with a hole for inserting the sample container T. The sample container T gripped by the hand portion 25a described above is moved after stirring is completed, and the gripped sample container T is inserted to the hole of the sample container setting portion 25b. Thereafter, the sample container T is released from the hand portion 25a by separating the gripping members, and the sample container T is set in the sample container setting portion 25b. The relevant sample container setting portion 25b is horizontally movable in the Y direction by the power of the stepping motor (not shown).

A barcode reading portion 26 is arranged inside the first measurement unit 2. The sample container setting portion 25b is movable to the barcode reading position 26a near the barcode reading portion 26 and the aspirating position 21a by the sample aspirating portion 21. When the sample container setting portion 25b is moved to the barcode reading position 26a, the set sample container T is horizontally rotated by a rotation mechanism (not shown), and the sample barcode is read by the barcode reading portion 26. Thus, even if the barcode label BL1 of the sample container T is positioned on the opposite side with respect to the barcode reading portion 26, the barcode label BL1 can be directed towards the barcode reading portion 26 by rotating the sample container T so that the sample barcode can be read by the barcode reading portion 26. When the sample container setting portion 25b is moved to the aspirating position, the sample is aspirated from the set sample container T by the sample aspirating portion 21.

The sample container setting portion 25b is movable to a priority sample setting position shown in FIG. 4 so as to project out to the front side as shown in FIG. 1B. The sample setting portion open/close button 27 is configured to be pushed by the operator or the service man when measuring the priority sample. When the sample setting portion open/close button 27 is pushed, the sample container setting portion 25b moves to the front side up to the priority sample setting position. The priority sample measurement start button 28 is configured to be pushed by the operator or the service man, and when the priority sample measurement button 28 is pushed, the sample container setting portion 25b set with the priority sample is taken into the first measurement unit 2 and the measurement is started.

The configuration of the second measurement unit 3 is the same as the configuration of the first measurement unit 2. The second measurement unit 3 includes a sample aspirating portion 31, a sample preparing portion 32 for preparing a measurement sample used in the measurement from the blood aspirated by the sample aspirating portion 31, and a detecting portion 33 for detecting the blood cell from the measurement sample prepared by the sample preparing portion 32. The second measurement unit 3 further includes a take-in port 34 (see FIGS. 1A and 1B) for taking in the sample container T accommodated in the sample rack L conveyed by the rack conveyance portion 43 of the sample conveyance unit 4 into the second measurement unit 3, and a sample container conveyance portion 35 for taking in the sample container T from the sample rack L into the second measurement unit 3 and conveying the sample container T to the aspirating position by the sample aspirating portion 31. The configurations of the sample aspirating portion 31, the sample preparing portion 32, the detecting portion 33, the take-in port 34, the sample container conveyance portion 35, and the barcode reading portion 36 are similar to the configurations of the sample aspirating portion 21, the sample preparing portion 22, the detecting portion 23, the take-in port 24, and the sample container conveyance portion 25, and thus the description thereof will be omitted.

<Configuration of Sample Conveyance Unit>

The configuration of the sample conveyance unit 4 will now be described. As shown in FIGS. 1A and 1B, the sample conveyance unit 4 is arranged on the front side of the first measurement unit 2 and the second measurement unit 3 of the sample analyzer 1. Such sample conveyance unit 4 can convey the sample rack L to supply the sample to the first measurement unit 2 and the second measurement unit 3.

Figure 6:
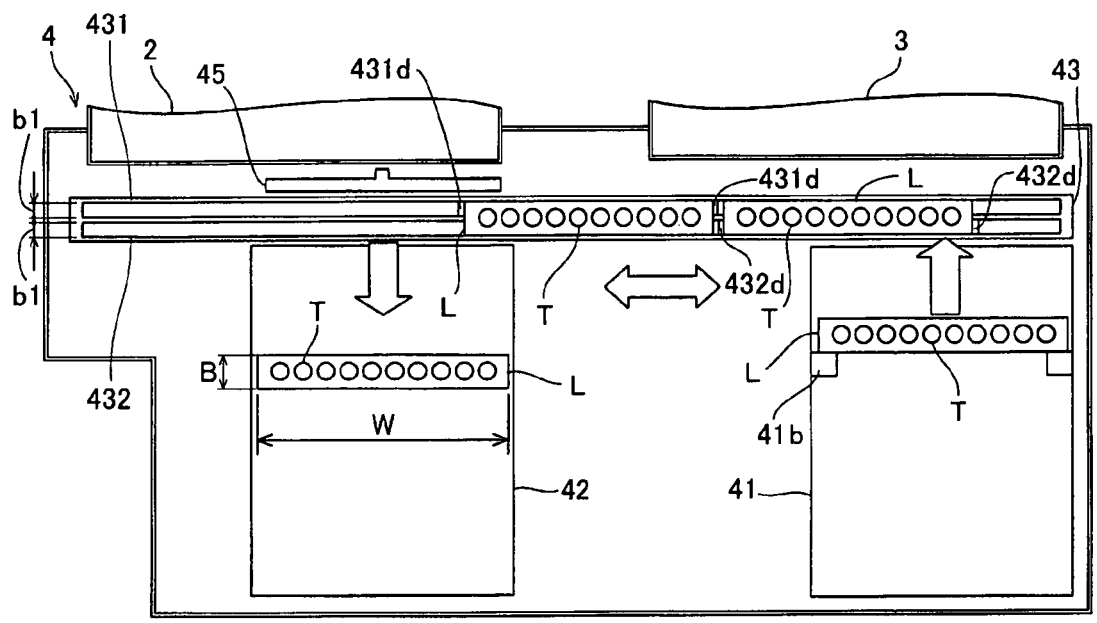
FIG. 6 is a plan view showing a configuration of the sample conveyance unit.

FIG. 6 is a plan view showing a configuration of the sample conveyance unit 4. As shown in FIG. 6, the sample conveyance unit 4 includes a pre-analysis rack holder 41 capable of temporarily holding a plurality of sample racks L for holding the sample container T accommodating the sample before the analysis, a post-analysis rack holder 42 capable of temporarily holding a plurality of sample racks L for holding the sample container T from which the sample is aspirated by the first measurement unit 2 or the second measurement unit 3, and a rack conveyance portion 43 for moving the sample rack L horizontally and linearly in the direction of the arrow X in the figure to supply the sample to the first measurement unit 2 or the second measurement unit 3, and conveying the sample rack L received from the pre-analysis rack holder 41 to the post-analysis rack holder 42.

The pre-analysis rack holder 41 has a square shape in plan view, which width is slightly larger than the width of the sample rack L. The pre-analysis rack holder 41 is formed to be one step lower than the peripheral surface, so that the sample rack L before the analysis is mounted on the upper surface thereof. A rack send-in portion 41b is arranged projecting towards the inner side from both side surfaces of the pre-analysis rack holder 41. The rack send-in portion 41b engages with the sample rack L by projecting out, and the sample rack L is moved to the back side when moved to the back side in such state (direction of approaching the rack conveyance portion 43). Such rack send-in portion 41b is configured to be drivable by a stepping motor (not shown) arranged on the lower side of the pre-analysis rack holder 41.

As shown in FIG. 6, the rack conveyance portion 43 can move the sample rack L moved by the pre-analysis rack holder 41 to the X direction. A first sample supply position 43a for supplying the sample to the first measurement unit 2 and a second sample supply position 43b for supplying the sample to the second measurement unit 3 shown in FIG. 4 are provided on the conveyance path of the sample rack L by the rack conveyance portion 43. Returning back to FIG. 4, the sample conveyance unit 4 is controlled by the information processing unit 5, wherein when the sample is conveyed to the first sample supply position 43a or the second sample supply position 43b, a hand portion 25a or 35a of the corresponding measurement unit grips the conveyed sample container T, takes out the sample container T from the sample rack L to thereby complete the supply of sample, and waits for the conveyance of the sample rack L until the sample container T is returned to the sample rack L. The hand portion 25a or 35a can reliably take out the sample container T from the sample rack L with the sample container T stopped at the first sample supply position 43a or the second sample supply position 43b. Furthermore, the rack conveyance portion 43 can convey the sample rack L to convey the sample container T to the sample container detection position 43c.

Figure 7:
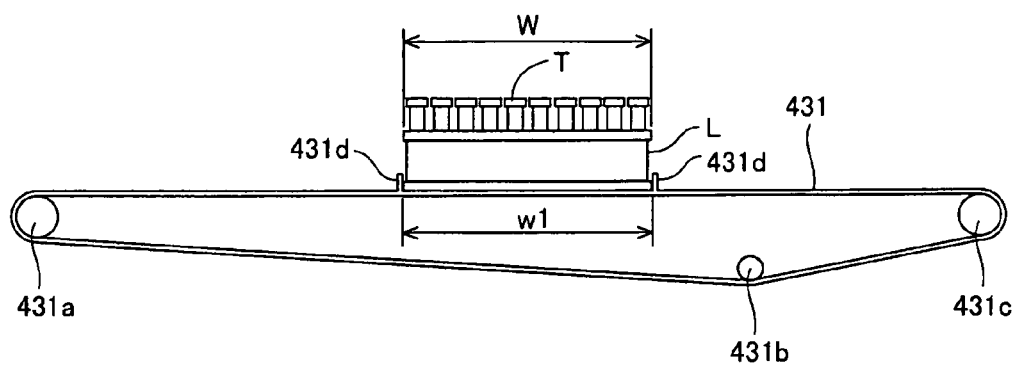
FIG. 7 is a front view showing a configuration of a first belt of the sample conveyance unit.
Figure 8:
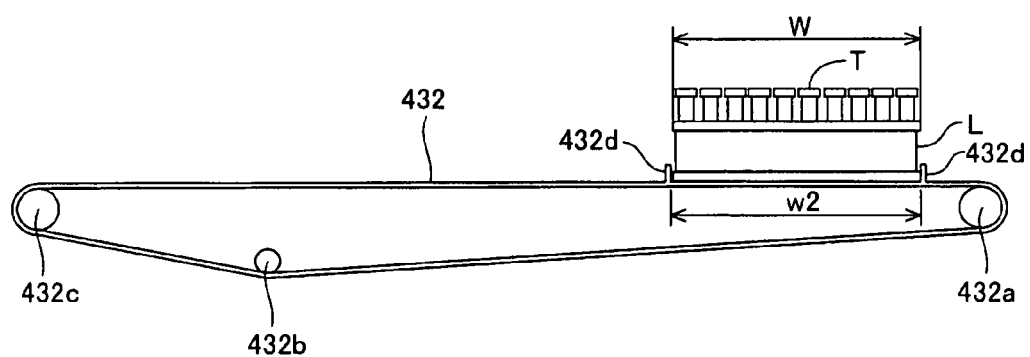
FIG. 8 is a front view showing a configuration of a second belt of the sample conveyance unit.

Proceeding to FIG. 6, the rack conveyance portion 43 includes two belts, a first belt 431 and a second belt 432, which are independently operable. The width b1 in the direction of the arrow Y of the first belt 431 and the second belt 432 is the size of smaller than or equal to half of the width B in the direction of the arrow Y of the sample rack L. Such first belt 431 and second belt 432 are arranged in parallel so as not to run out from the width B of the sample rack L when the rack conveyance portion 43 conveys the sample rack L. FIG. 7 is a front view showing a configuration of the first belt 431, and FIG. 8 is a front view showing a configuration of the second belt 432. As shown in FIGS. 7 and 8, the first belt 431 and the second belt 432 are formed to an annular shape, wherein the first belt 431 is arranged to surround rollers 431a to 431c and the second belt 432 is arranged to surround rollers 432a to 432c. Two projecting pieces 431d having an inner width w1 slightly (e.g., 1 mm) larger than the width W in the X direction of the sample rack L are arranged on the outer peripheral part of the first belt 431, and similarly, two projecting pieces 432d having an inner width w2 of the same extent as the inner width w1 are arranged on the outer peripheral part of the second belt 432. The first belt 431 is configured to move the sample rack L in the direction of the arrow X by being moved at the outer periphery of the rollers 431a to 431c by the stepping motor (not shown) while holding the sample rack L on the inner side of the two projecting pieces 431d. The second belt 432 is configured to move the sample rack L in the direction of the arrow X by being moved at the outer periphery of the rollers 432a to 432c by the stepping motor (not shown) while holding the sample rack L on the inner side of the two projecting pieces 452d. The first belt 431 and the second belt 432 are also configured to move the sample rack independently of each other.

Returning to FIG. 4, a sample container sensor 44 is a contact-type sensor, and includes contact piece of curtain shape, a light emitting element for emitting light, and a light receiving element (not shown). The sample container sensor 44 is configured such that the contact piece is bent by contacting the detecting object of the detection target, and as a result, the light emitted from the light emitting element is reflected by the contact piece and received by the light receiving element. Therefore, when the sample container T of the detection target accommodated in the sample rack L passes below the sample container sensor 44, the contact piece is bent by the sample container T, and the sample container T is detected.

The rack sending portion 45 is arranged to face the post-analysis rack holder 42, to be hereinafter described, with the rack conveyance portion 43 in between. The rack sending portion 45 is configured to move horizontally and linearly in the direction of the arrow Y by the driving force of the stepping motor (not shown). Thus, when the sample rack L is conveyed to a position 451 (hereinafter referred to as "post-analysis rack sending position") between the post-analysis rack holder 42 and the rack sending portion 45, the rack sending portion 45 is moved to the post-analysis rack holder 42 side so that the sample rack L can be pushed and moved into the post-analysis rack holder 42.

The post-analysis rack holder 42 has a square shape in plan view, which width is slightly larger than the width of the sample rack L. The post-analysis rack holder 42 is formed to be one step lower than the peripheral surface so that the sample rack L, which analysis is completed, is mounted on the upper surface thereof. The post-analysis rack holder 42 is connected to the rack conveyance portion 43, so that the sample rack L is sent from the rack conveyance portion 43 by the rack sending portion 45.

According to such configuration, the sample conveyance unit 4 moves the sample rack L mounted on the pre-analysis rack holder 41 to the rack conveyance portion 43, and further conveys the same by the rack conveyance portion 43, so that the sample can be supplied to the first measurement unit 2 or the second measurement unit 3. The sample rack L accommodating the sample, which aspiration is completed, is moved to the post-analysis rack sending position (not shown) by the rack conveyance portion 43, and sent to the post-analysis rack holder 42 by the rack sending portion 45. If a plurality of sample racks L are mounted on the pre-analysis rack holder 41, the sample rack L accommodating the sample, which analysis is completed, is sequentially sent to the post-analysis rack holder 42 by the rack sending portion 45, and such sample racks L are stored in the post-analysis rack holder 42.

<Configuration of Information Processing Unit>

Figure 9:
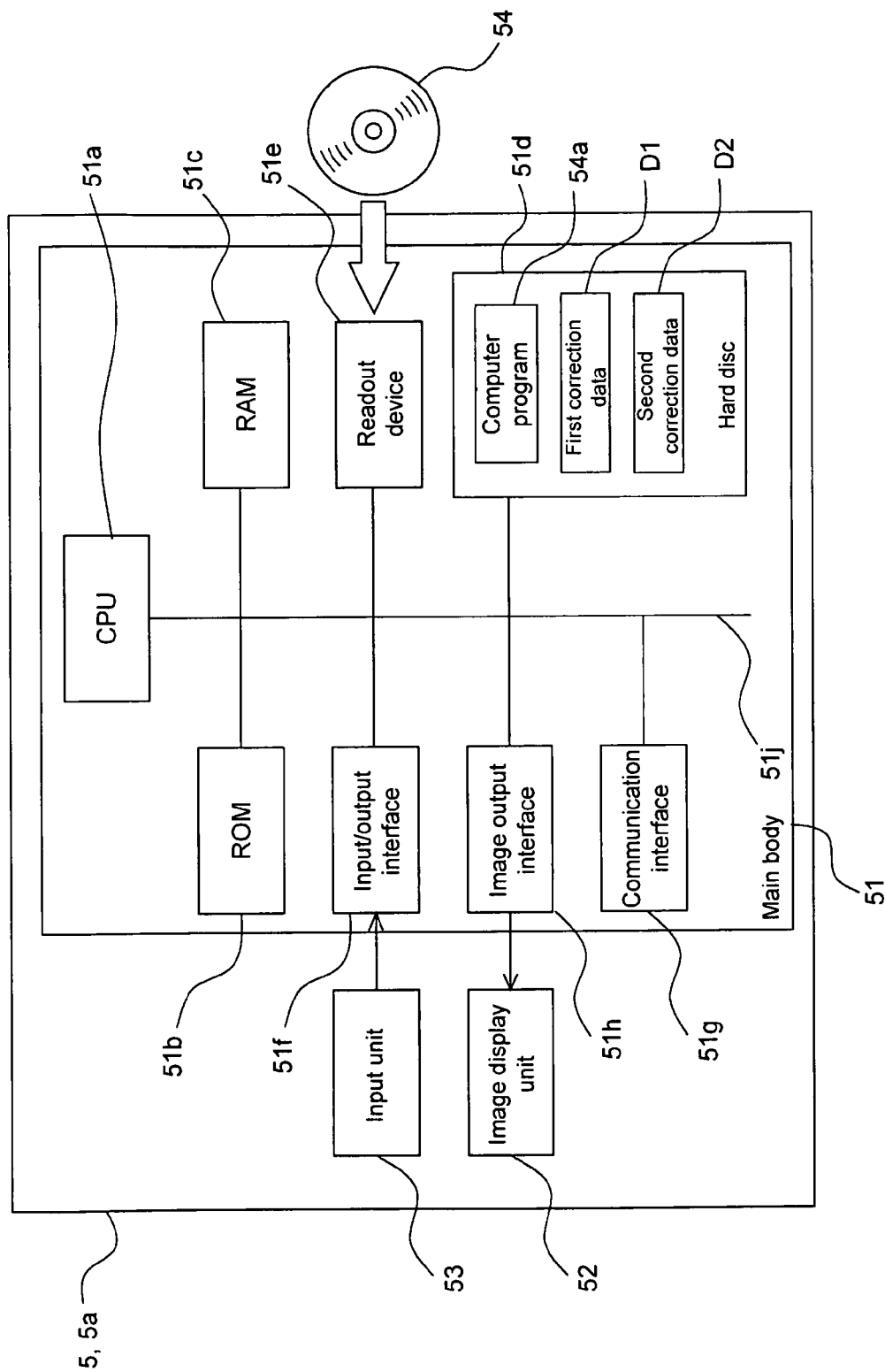
FIG. 9 is a block diagram showing a configuration of the information processing unit according to the embodiment.

The configuration of the information processing unit 5 will now be descried. The information processing unit 5 is configured by a computer. FIG. 9 is a block diagram showing a configuration of the information processing unit 5. The information processing unit 5 is realized by a computer 5a. As shown in FIG. 9, the computer 5a includes a main body 51, an image display unit 52, and an input unit 53. The main body 51 includes a CPU 51a, a ROM 521b, a RAM 51c, a hard disc 51d, a readout device 51e, an input/output interface 51f, a communication interface 51g, and an image output interface 51h, wherein the CPU 51a, the ROM 51b, the RAM 51c, the hard disc 51d, the readout device 51e, the input/output interface 51f, the communication interface 51g, and the image output interface 51h are connected by a bus 51j.

The CPU 51a can execute the computer program loaded in the RAM 51c. The computer 5a functions as the information processing unit 5 when the CPU 51a executes a computer program 54a for sample analysis and for control of the first measurement unit 2, the second measurement unit 3, and the sample conveyance unit 4, to be hereinafter described.

The ROM 51b is configured by mask ROM, PROM, EPROM, EEPROM, and the like, and is recorded with the computer program executed by the CPU 51a, the data used when executing the computer program, and the like.

The RAM 51c is configured by SRAM, DRAM, or the like. The RAM 51c is used to read out the computer program 54a recorded in the hard disc 51d. The RAM 51c is used as a work region of the CPU 51a when the CPU 51a executes such computer programs.

The hard disc 51d is installed with various computer programs to be executed by the CPU 51a, and the data used for the execution of the computer program, such as an operating system and an application program. The computer program 54a to be hereinafter described is also installed in the hard disc 51d.

The hard disc 51d is also stored with first correction data D1 for correcting the analysis result generated from the measurement data of the first measurement unit 2, and second correction data D2 for correcting the analysis result generated from the measurement data of the second measurement unit 2.

The readout device 51e is configured by flexible disc drive, CD-ROM drive, DVD-ROM, or the like. The readout device 51e can read out computer program or data recorded in a portable recording medium 54. The portable recording medium 54 stores the computer program 54a for causing the computer to function as the information processing unit 5, wherein the computer 5a reads out the computer program 54a from the portable recording medium 54, and installs the computer program 54a in the hard disc 51d.

The computer program 54a is not limited to being provided by the portable recording medium 54, and may be provided through an electrical communication line from an external device communicably connected to the computer 5a by the electrical communication line (wired or wireless). For instance, the computer program 54a may be stored in a hard disc of a server computer on the Internet, and the computer 5a may access the server computer, and download the computer program and store the same in the hard disc 51d.

The hard disc 51d is installed with a multi-task operating system such as Windows (registered trademark) manufactured and sold by U.S. Microsoft Co. In the following description, the computer program 54a according to the present embodiment is assumed to operate on the operating system.

The input/output interface 51f is configured by serial interface such as USB, IEEE 1394, RS-232C; parallel interface such as SCSI, IDE, IEEE 1284; analog interface including D/A converter, A/D converter and the like. The input/output interface 51f is connected with the input unit 53 such as a keyboard and a mouse, and the user can input data to the computer 5a by using the input unit 53. The input/output interface 51f is connected to the first measurement unit 2, the second measurement unit 3, and the sample conveyance unit 4. The information processing unit 5 thus can control the first measurement unit 2, the second measurement unit 3, and the sample conveyance unit 4.

The communication interface 51g is an Ethernet (registered trademark) interface. The communication interface 51g is connected to a host computer (not shown) through the LAN. The computer 5a can transmit and receive data with the host computer connected to the LAN using a predetermined communication protocol by the communication interface 51g.

The image output interface 51h is connected to the image display unit 52 configured by LCD, CRT, or the like, and outputs a video signal corresponding to the image data provided from the CPU 51a to the image display unit 52. The image display unit 52 displays an image (screen) according to the input video signal.

[Operation of Sample Analyzer 1]

The operation of the sample analyzer 1 according to the present embodiment will be described below.

<Automatic Calibration Operation>

First, the automatic calibration operation in which the sample analyzer 1 according to the present embodiment automatically performs the calibration of the first measurement unit 2 and the second measurement unit 3 will be described. The automatic calibration operation includes automatically performing a series of operations of automatically conveying the sample rack L inserted with the sample container T of the calibrator and the sample container T of the sample for reproducibility check or the normal sample at a predetermined position (holding position 1 and holding position 2 in the present embodiment), checking the reproducibility of the analysis result of the first measurement unit 2 before the calibration by the sample for reproducibility check, performing calibration of the first measurement unit 2 by the calibrator, checking the reproducibility of the analysis result of the second measurement unit 2 before the calibration by the sample for reproducibility check, and performing the calibration of the second measurement unit 3. The calibrator is a sample which concentration of the component is known, wherein the calibration of the measurement unit is performed by defining the correction value (correction data) of the analysis result so that the numerical value of the analysis result of the calibrator matches the concentration (hereinafter referred to as "reference concentration"). The normal sample is usually used for the sample for reproducibility check.

Figure 10:
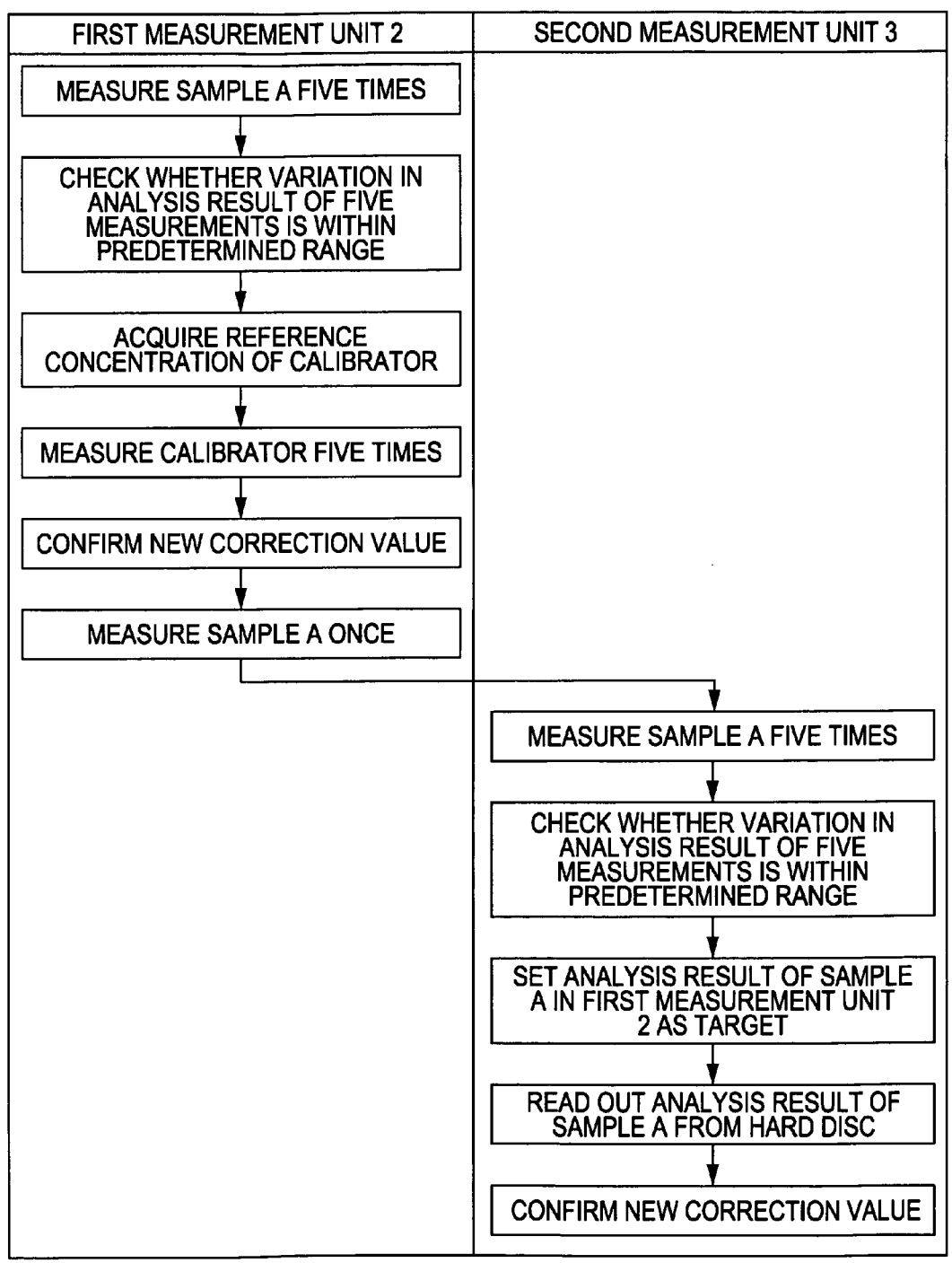
FIG. 10 is a view describing an outline of a procedure of the automatic calibration operation of the sample analyzer according to the embodiment.

FIG. 10 is a view describing an outline of a procedure of the automatic calibration operation of the sample analyzer 1. As shown in the figure, in the automatic calibration operation of the sample analyzer 1 according to the present embodiment, the same sample A is first measured continuously five times by the first measurement unit 2, and whether the variation in the analysis result by the five measurements is within a predetermined range is checked (reproducibility check). Thereafter, the reference concentration of the calibrator is input to the sample analyzer 1, the calibrator is measured five times by the first measurement unit 2, and the correction value of the first measurement unit 2 is calculated by the analysis result of the calibrator and the reference concentration. Thereafter, the sample A is again measured once by the first measurement unit 2, and the analysis result by a new correction value is calculated. Subsequently, the sample A is measured five times by the second measurement unit 3, and whether the variation in the analysis result by five measurements is within a predetermined range is checked. The reproducibility check of the analysis result of the second measurement unit 3 is carried out in such manner. The analysis result obtained by the measurement of the sample A of the first measurement unit 2 after the calculation of the correction value is then set as a target value (reference concentration) of the calibration of the second measurement unit 3, the analysis result by five measurements of the sample A of the second measurement unit 3 is read out from the hard disc 51d, and the correction value of the second measurement unit 3 is calculated by the analysis result and the target value. The outline of the procedure of the automatic calibration operation is as described above.

Figure 11:
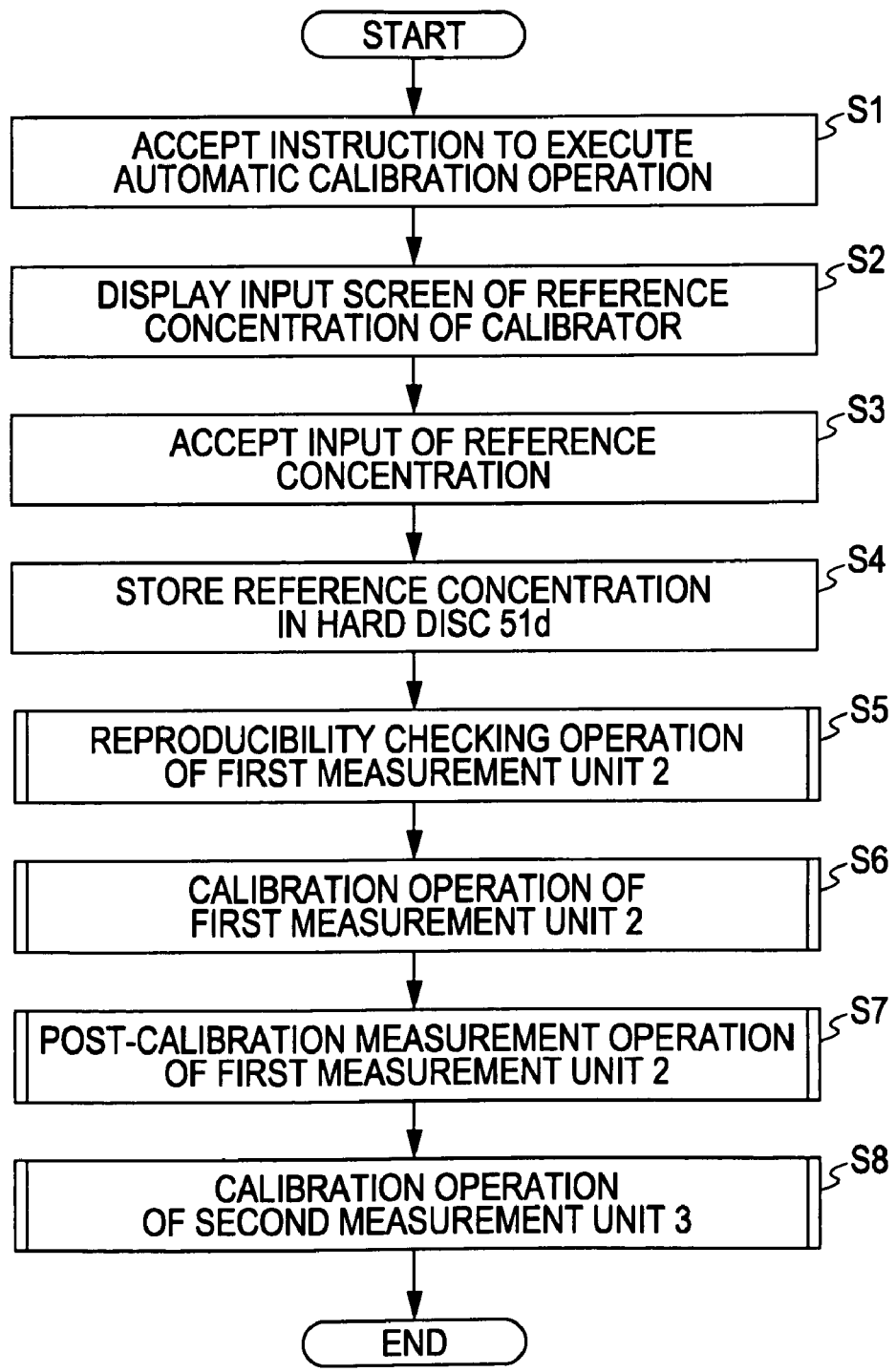
FIG. 11 is a flowchart showing a flow of process of the CPU of the information processing unit in the automatic calibration operation.

The automatic calibration operation of the sample analyzer 1 will be specifically described below. FIG. 11 is a flowchart showing a flow of process of the CPU 51a in the automatic calibration operation of the sample analyzer 1. The operator inserts the sample container T accommodating the calibrator to the holding position 1 of the sample rack L, inserts the sample container T accommodating the sample for reproducibility check of human blood to the holding position 2, and places on the pre-analysis rack holder 41. In this state, the operator operates the input unit 53 and instructs the execution of the automatic calibration operation to the information processing unit 5. The computer program 54a executed by the CPU 51a of the information processing unit 5 is an event-driven type program, wherein the process of step S2 is called out when an event of accepting the instruction to execute the automatic calibration operation occurs (step S1) in the CPU 51a.

In step S2, the CPU 51a displays an input screen (not shown) of the reference concentration of the calibrator (step S2). This screen includes an input region to which the reference concentration of the calibrator can be input, and the operator operates the input unit 53 to input the reference concentration written on the packaging box or the like of the calibrator to the information processing unit 5. When an event of accepting the input of the reference concentration occurs (step S3), the CPU 51a stores the reference concentration in the hard disc 51d (step S4). The CPU 51a executes the reproducibility checking operation of the first measurement unit 2 of measuring the sample for reproducibility check by the first measurement unit 2 (step S5), executes the calibration operation of the first measurement unit 2 of measuring the calibrator by the first measurement unit 2 (step S6), and executes the post-calibration measurement operation of measuring the sample for reproducibility check by the first measurement unit 2 (step S7). The CPU 51a then executes the calibration operation of the second measurement unit 3 of measuring the sample for reproducibility check by the second measurement unit 3 (step S8), and thereafter terminates the process.

Figure 12:
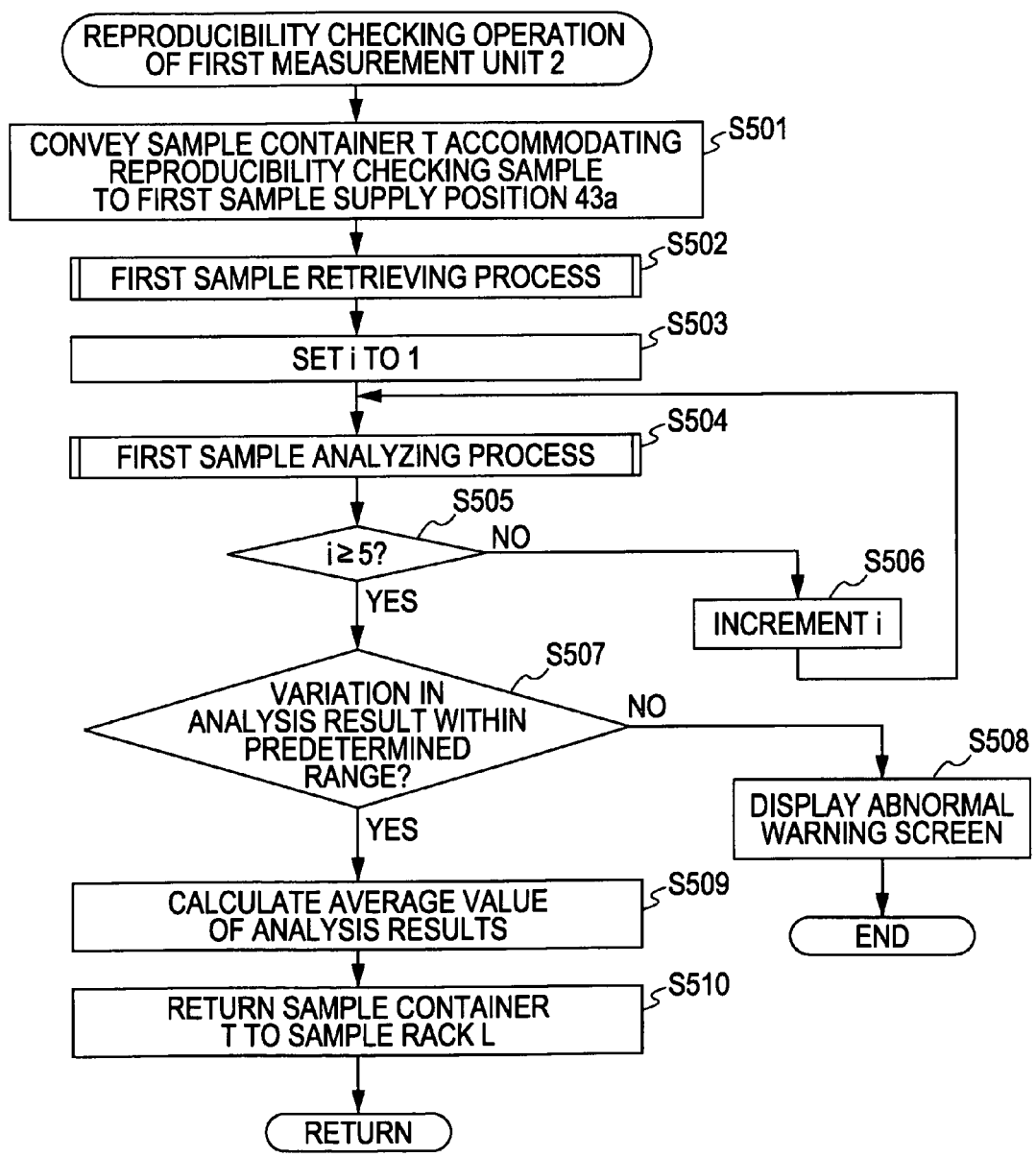
FIG. 12 is a flowchart showing a flow of the reproducibility checking process of the first measurement unit by the CPU of the information processing unit.

The reproducibility checking operation of the first measurement unit 2 will be described in detail below. The reproducibility checking operation of the first measurement unit 2 is an operation of measuring the sample for reproducibility check before the calibration of the first measurement unit 2 and acquiring the analysis result of the sample for reproducibility check to check the reproducibility of the analysis result before the calibration of the first measurement unit 2. FIG. 12 is a flowchart showing a flow of the reproducibility checking operation of the first measurement unit 2. First, the CPU 51a controls the sample conveyance unit 4 to move the sample rack L to the pre-analysis rack holder 41, convey the sample rack L on the rack conveyance portion 43, and convey the holding position 2 of the sample rack L, that is, the sample container T accommodating the sample for reproducibility check to the first sample supply position 43a (step S51).

Figure 13:
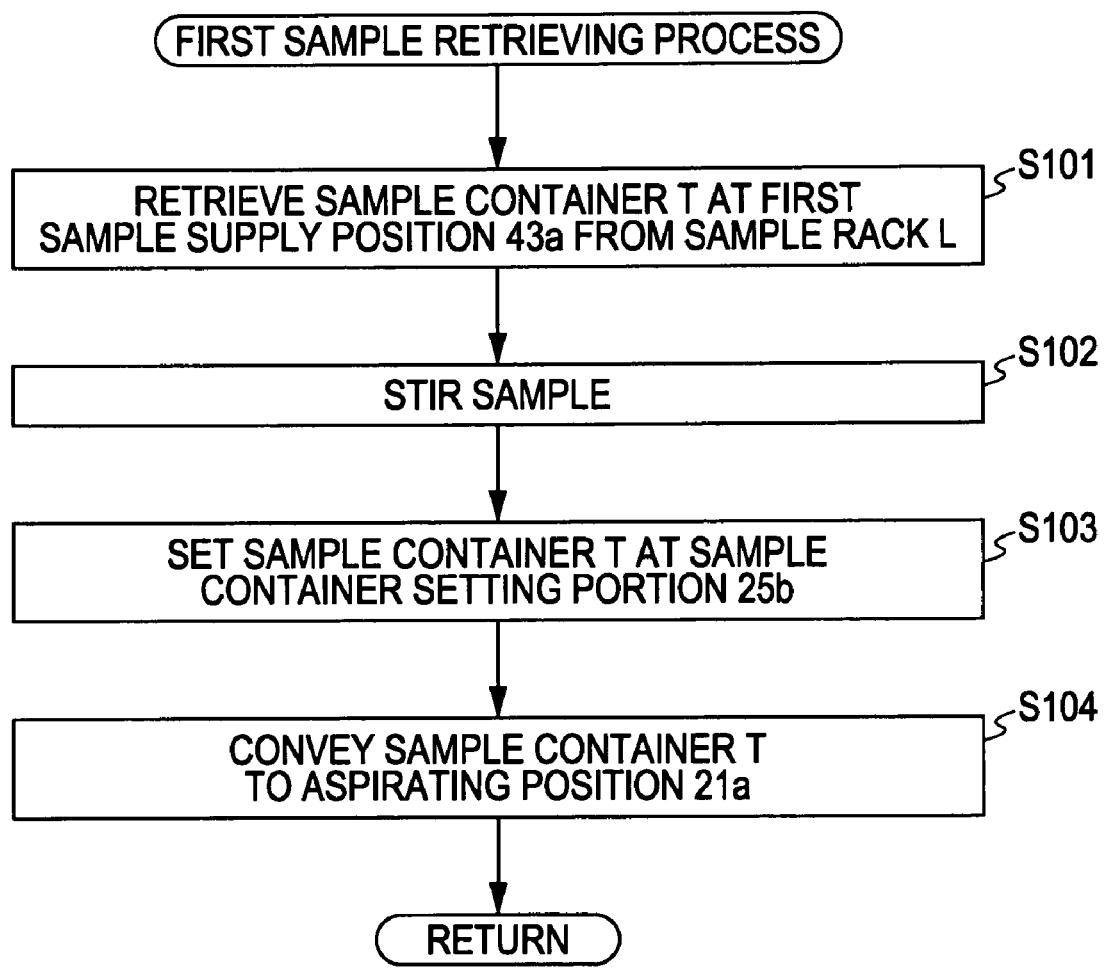
FIG. 13 is a flowchart showing a procedure of a first sample retrieving process by the CPU of the information processing unit.

The CPU 51a executes the first sample retrieving process of retrieving the sample into the first measurement unit 2 from the sample container T at the first sample supply position 43a (step S52). FIG. 13 is a flowchart showing a procedure of the first sample retrieving process by the CPU 51a of the information processing unit 5. The CPU 51a controls the sample container conveyance portion 25 to take out the sample container T at the first sample supply position 43a from the sample rack L (step S101), and controls the hand portion 25a to oscillate the sample container T and stir the sample inside (step S102). The CPU 51a then controls the hand portion 25a and sets the sample container T at the sample container setting portion 25b (step S103), and also controls the sample container conveyance portion 25 to convey the sample container T to the aspirating position (step S104). After the process of step S104 is completed, the CPU 51a returns the process to the call out address of the first sample retrieving process.

Returning back to FIG. 12, after the first sample retrieving process S52 is terminated, the CPU 51a sets the variable i indicating the number of measurements to 1 (step S53), and executes a first sample analyzing process of measuring the sample with the first measurement unit 2 (step S54).

Figure 14:
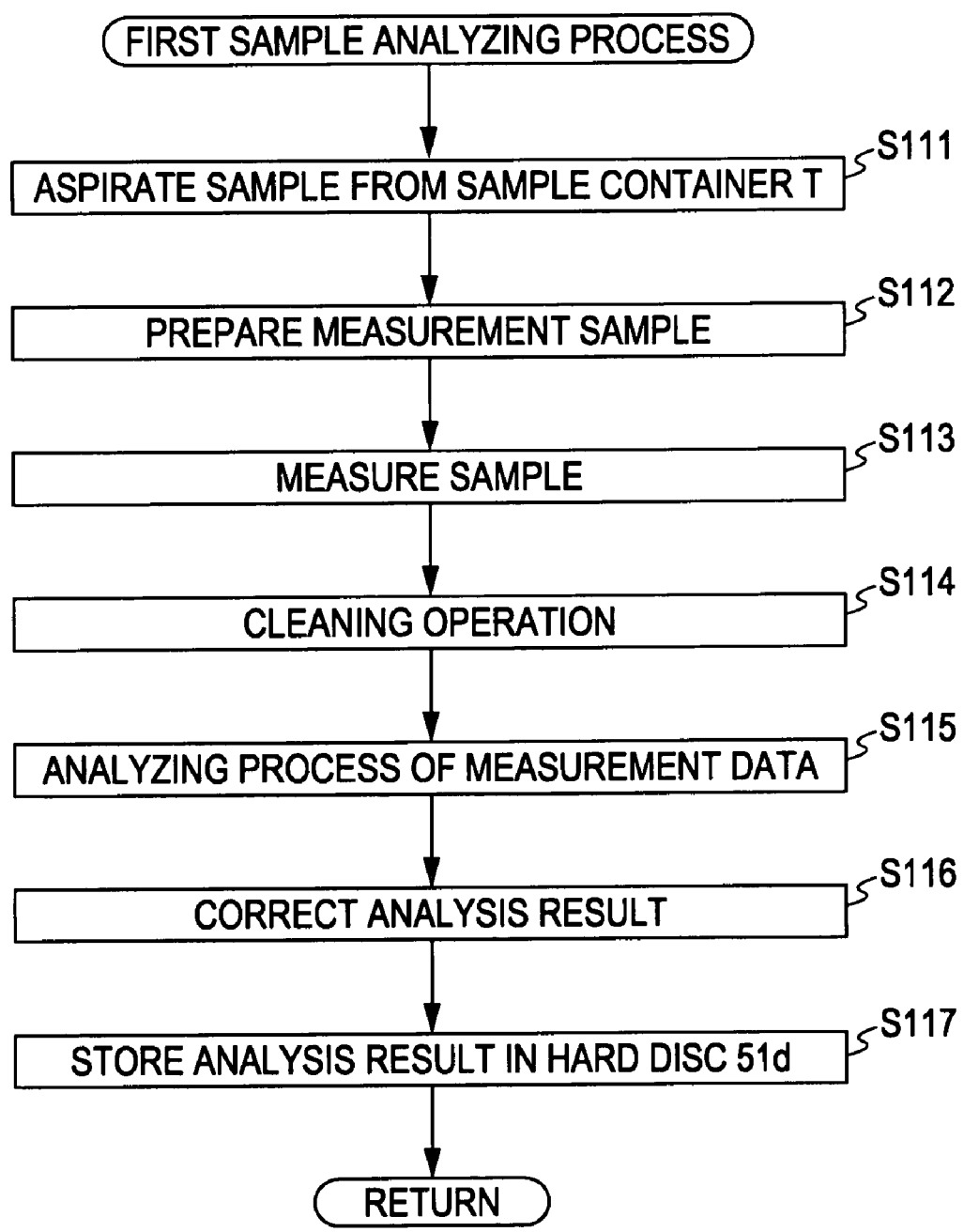
FIG. 14 is a flowchart showing a procedure of a first sample analyzing process by the CPU of the information processing unit.

FIG. 14 is a flowchart showing a procedure of the first sample analyzing process by the CPU 51a of the information processing unit 5. The CPU 51a controls the sample aspirating portion 21 to aspirate the sample of an amount necessary for the measurement from the sample container T (step S111). After the aspiration of the sample is completed, the CPU 51a controls the sample preparing portion 22 to prepare the measurement sample (step S112), supplies the measurement sample to the detecting portion 23, and performs the measurement of the sample by the detecting portion 23 (step S113). The CPU 51a thereby acquires the measurement data output from the detecting portion 23. The CPU 51a then executes a cleaning operation of cleaning a flow path, a reaction chamber, and the like used in the measurement (step S114).

The CPU 51a executes the analyzing process of the measurement data (step S115), and obtains the analysis result including the numerical values and the like of RBC, PLT, HGB, WBC, NEUT, LYMPH, EO, BASO, and MONO. The CPU 51a then corrects the analysis result with the correction data (first correction data D1 for the measurement data of the first measurement unit 2, second correction data D2 for the measurement data of the second measurement unit 3) stored in the hard disc 51d (step S116). The corrected analysis result data is stored in the hard disc 51d (step S117). After the process of step S117 is completed, the CPU 51a returns the process to the call out address of the first sample analyzing process.

Returning back to FIG. 12, after the first sample analyzing process S54 is terminated, the CPU 51a determines whether or not i is greater than or equal to five (step S55). If i is smaller than five (NO in step S55), the CPU 51a increments by one (step S56), and returns the process to step S54. The sample for reproducibility check is thereby measured five times by the first measurement unit 2.

If i is greater than or equal to five in step S55 (YES in step S55), the CPU 51a reads out the analysis result of the sample for reproducibility check obtained through five measurements from the hard disc 51d, and determines whether or not the variation in five analysis results is within a predetermined range, that is, the difference of the minimum value and the maximum value of the five analysis results is within a predetermined range (step S57). If the variation in five analysis results exceeds the predetermined range (NO in step S57), the first measurement unit 2 is assumed to be abnormal, and thus the CPU 51a displays an abnormal warning screen on the image display unit 52 (step S58), and terminates the process.

If the variation in five analysis results is within the predetermined range in step S57 (YES in step S57), the CPU 51a calculates an average value of the analysis results, and stores the same in the hard disc 51d (step S59). Thereafter, the CPU 51a controls the sample container conveyance portion 25 to return the sample container T accommodating the sample for reproducibility check back to the sample rack L (step S510), and returns the process to the call out address of the reproducibility checking operation of the first measurement unit 2.

After the reproducibility checking operation of the first measurement unit 2, the calibration operation (step S6) of the first measurement unit 2 is executed. The calibration operation of the first measurement unit 2 will be described in detail below. The calibration operation of the first measurement unit 2 is an operation of measuring the calibrator by the first measurement unit 2, and updating the first correction data D1 used to correct the analysis result obtained from the measurement result by the first measurement unit 2.

Figure 15:
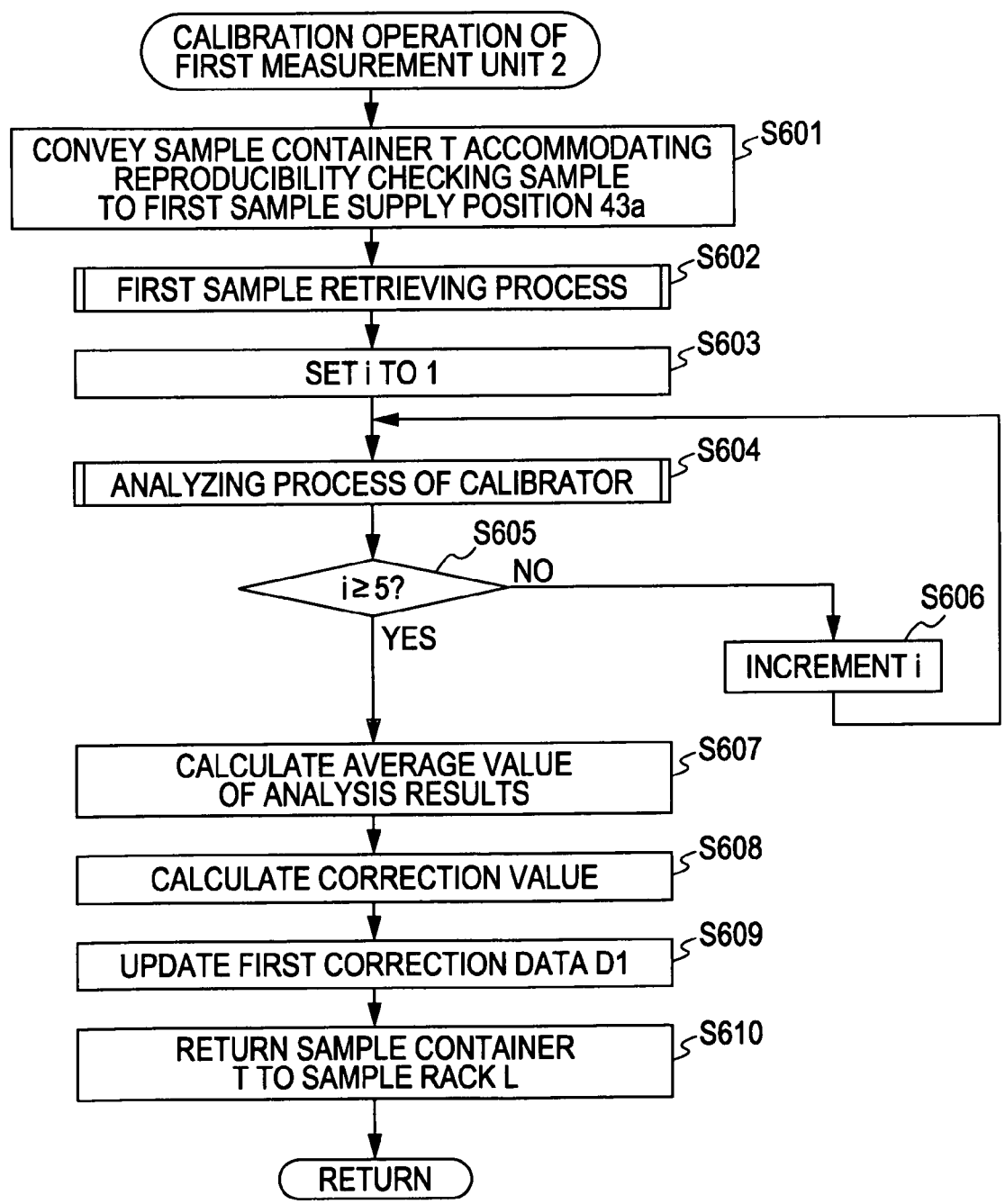
FIG. 15 is a flowchart showing a flow of a calibration operation of the first measurement unit by the CPU of the information processing unit.

FIG. 15 is a flowchart showing a flow of the calibration operation of the first measurement unit 2. First, the CPU 51a controls the sample conveyance unit 4 to convey the sample rack L on the rack conveyance portion 43, and conveys the holding position 1 of the sample rack L, that is, the sample container T accommodating the calibrator to the first sample supply position 43a (step S601). The CPU 51a executes the first sample retrieving process (see FIG. 13) similar to step S52 (step S602).

After the first sample retrieving process S602 is terminated, the CPU 51a sets the variable i indicating the number of measurements to 1 (step S603), and executes an analyzing process of the calibrator (step S604). The analyzing process of the calibrator is similar to the first sample analyzing process other than measuring the calibrator in place of the sample, and thus the description thereof will be omitted.

After the calibrator analyzing process S604 is terminated, the CPU 51a determines whether or not i is greater than or equal to five (step S605). If i is smaller than five (NO in step S605), the CPU 51a increments i by one (step S606), and returns the process to step S604. The calibrator is measured five times by the first measurement unit 2.

If i is greater than or equal to five in step S605 (YES in step S65), the CPU 51a reads out the analysis result of the calibrator obtained through five measurements from the hard disc 51d, calculates the average value of such analysis results (step S607), and calculates a correction value based on the average value and the reference concentration (step S608). In this process, the correction value is obtained with the following equation.

New correction value=current correction value×(average value of analysis results of reference concentration/calibrator)

The CPU 51a then updates the first correction data D1 with the new correction value (step S609). Furthermore, the CPU 51a controls the sample container conveyance portion 25 to return the sample container T accommodating the calibrator to the sample rack L (step S610), and returns the process to the call out address of the calibration operation of the first measurement unit 2.

Figure 16:
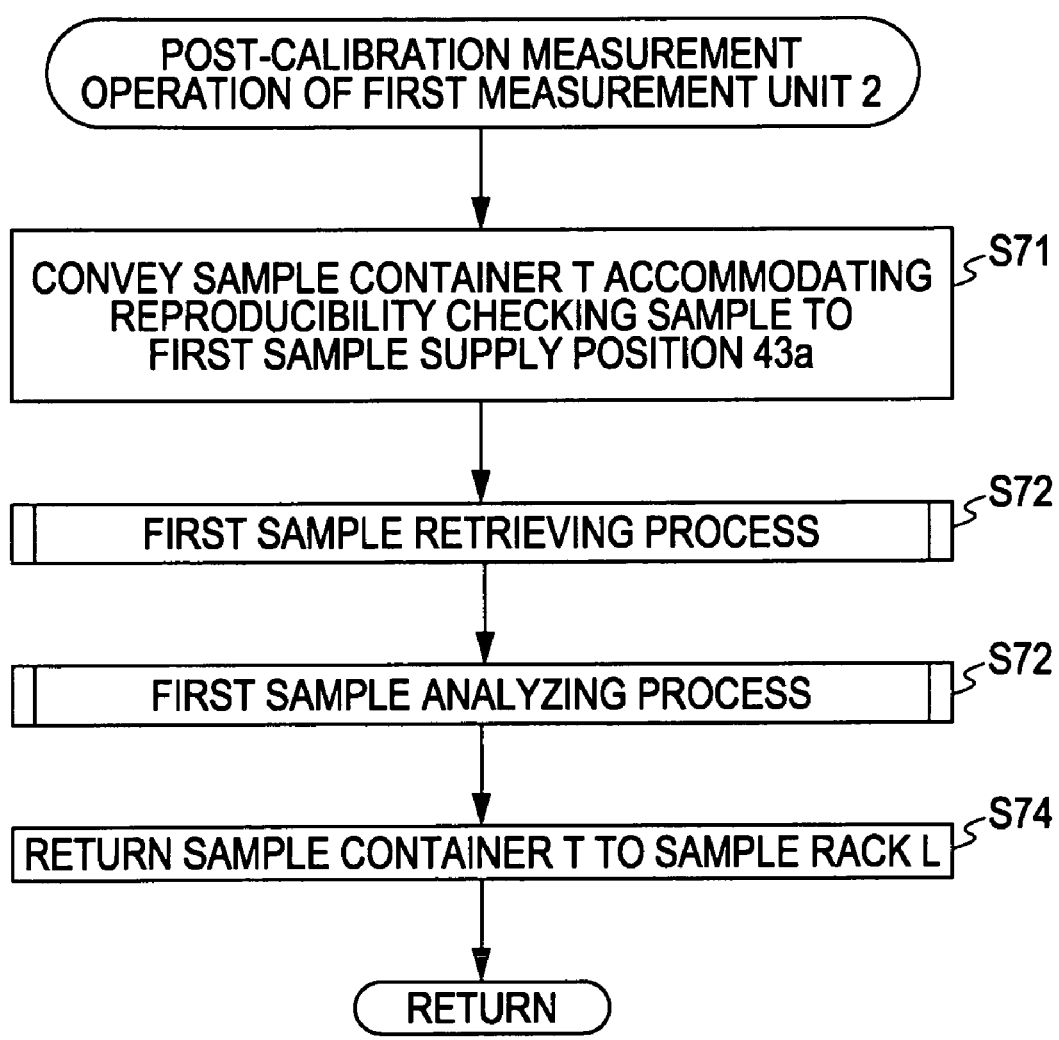
FIG. 16 is a flowchart showing a flow of a post-calibration process of the first measurement unit by the CPU of the information processing unit.

After the calibration operation of the first measurement unit 2, the post-calibration measurement operation (step S7) is executed. The post-calibration measurement operation will be described in detail below. The post-calibration measurement operation is an operation of measuring the sample for reproducibility check after the calibration of the first measurement unit 2, and acquiring the analysis result of the sample for reproducibility check. FIG. 16 is a flowchart showing a flow of the post-calibration measurement operation. The CPU 51a controls the sample conveyance unit 4 to convey the sample rack L on the rack conveyance portion 43, and again convey the holding position 2 of the sample rack L, that is, the sample container T accommodating the sample for reproducibility check to the first sample supply position 43a (step S71). The CPU 51a executes the first sample retrieving process, similar to step S52 (step S72).

After the first sample retrieving process S72 is terminated, the CPU 51a executes the first sample analyzing process, similar to step S54, once (step S73). In the first sample analyzing process, the analysis result is corrected using the updated first correction data D1, and the corrected analysis result is stored in the hard disc 51d.

Thereafter, the CPU 51a controls the sample container conveyance portion 25 to return the sample container T accommodating the sample for reproducibility check to the sample rack L (step S74), and returns the process to the call out address of the post-calibration measurement operation.

Figure 17:
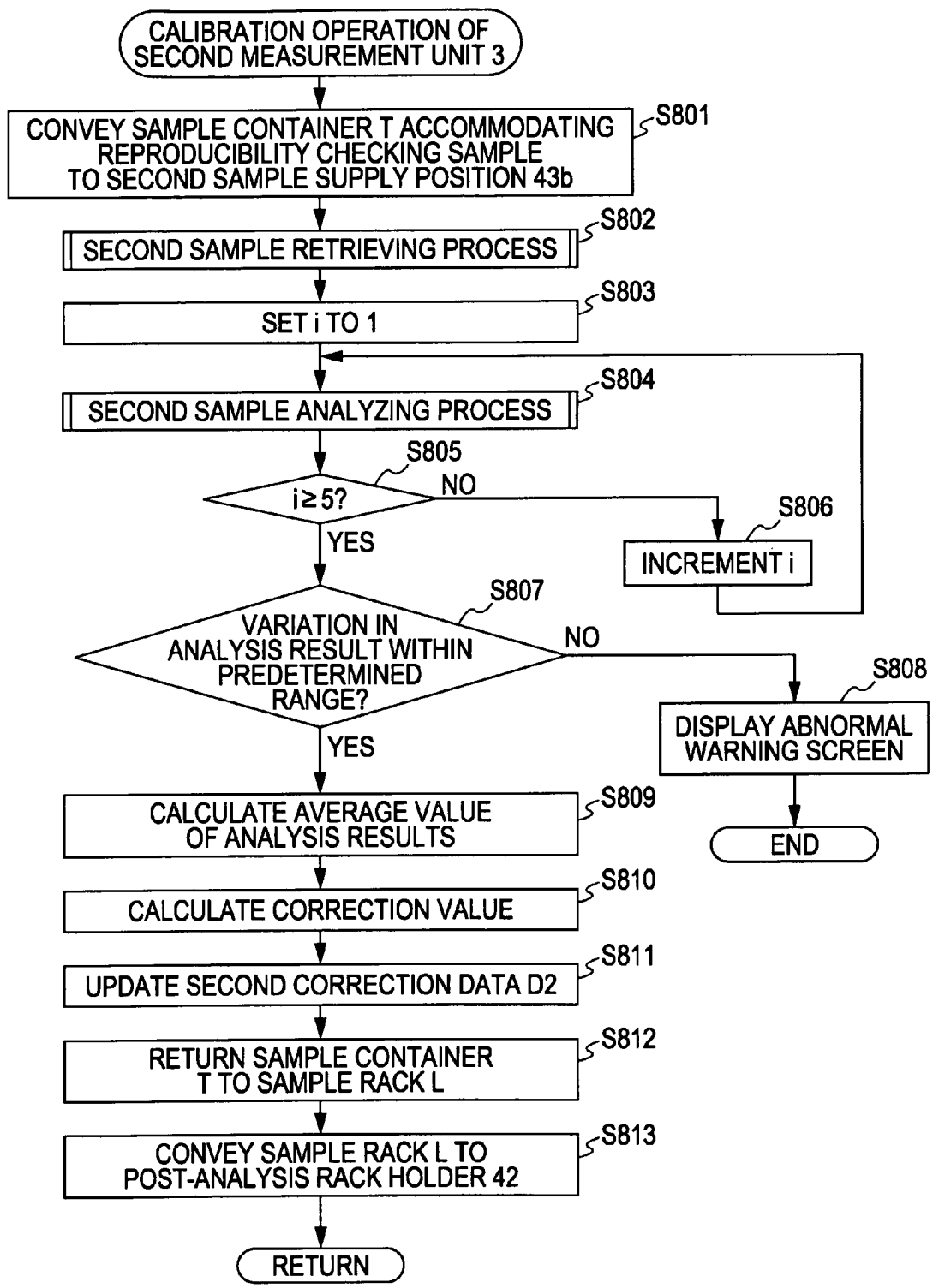
FIG. 17 is a flowchart showing a flow of a calibration operation of the second measurement unit by the CPU of the information processing unit.

After such post-calibration measurement operation, the calibration operation of the second measurement unit 3 (step S8) is executed. The calibration operation of the second measurement unit 3 will be described in detail below. The calibration operation of the second measurement unit 3 is an operation of measuring the sample for reproducibility check before the calibration of the second measurement unit 3 and acquiring the analysis result of the sample for reproducibility check to check the reproducibility of the analysis result of before the calibration of the second measurement unit 3, and is an operation of updating the second correction data D2 used to correct the analysis result obtained from the measurement result by the second measurement unit 3. FIG. 17 is a flowchart showing a flow of the calibration operation of the second measurement unit 3. First, the CPU 51a controls the sample conveyance unit 4 to convey the sample rack L on the rack conveyance portion 43, and convey the holding position 2 of the sample rack L, that is, the sample container T accommodating the sample for reproducibility check to the second sample supply position 43b (step S801).

The CPU 51a then executes a second sample retrieving process of retrieving the sample into the second measurement unit 3 from the sample container T at the second sample supply position 43b (step S802). The second sample retrieving process S802 is performed by having the second measurement unit 3 perform the operation similar to the first sample retrieving process S52 performed by the first measurement unit 2 of the same configuration, and thus the description thereof will be omitted.

After the second sample retrieving process S802 is terminated, the CPU 51a sets the variable i indicating the number of measurements to one (step S803), and executes the second sample analyzing process for measuring the sample by the second measurement unit 2 (step S804). The second sample analyzing process is similar to the first sample analyzing process of step S54 other than that the sample is measured by the second measurement unit 3 in place of the first measurement unit 2, and thus the description will be omitted.

After the second sample analyzing process S804 is terminated, the CPU 51a determines whether or not i is greater than or equal to five (step S805). If i is smaller than five (NO in step S805), the CPU 51a increments i by one (step S806), and returns the process to step S804. The sample for reproducibility check is thereby measured five times by the second measurement unit 3.

If i is greater than or equal to five in step S805 (YES in step S805), the CPU 51a reads out the analysis result after the correction of the sample for reproducibility check obtained through five measurements from the hard disc 51d, and determines whether or not the variation in five analysis results is within a predetermined range, that is, the difference of the minimum value and the maximum value of the five analysis results is within a predetermined range (step S807). If the variation in five analysis results exceeds the predetermined range (NO in step S807), the second measurement unit 3 is assumed to be abnormal, and thus the CPU 51a displays the abnormal warning screen on the image display unit 52 (step S808), and terminates the process.

If the variation in five analysis results is within the predetermined range in step S57 (YES in step S807), the CPU 51a calculates an average value of the analysis results (step S809). The CPU 51a reads out from the hard disc 51d the analysis result of the sample for reproducibility check by the first measurement unit 2 after calibration stored in the hard disc 51d in the post-calibration measurement operation S7, and calculates the correction value based on the average value and the reference concentration, with the analysis result as the reference concentration (step S810). In this process, the correction value is obtained through the following equation.

New correction value=current correction value×(average value of analysis result obtained in S73/analysis result of sample for reproducibility check by second measurement unit.

The CPU 51a then updates the second correction data D2 with such correction value (step S811). Thereafter, the CPU 51a controls the sample container conveyance portion 25 to return the sample container T accommodating the sample for reproducibility check to the sample rack L (step S812), controls the sample conveyance unit 4 to convey the sample rack L to the post-analysis rack holder 42 (step S813), and returns the process to the call out address of the calibration operation of the second measurement unit 3.

According to the automatic calibration operation described above, the calibration of the first measurement unit 2 and the second measurement unit 3 are automatically performed by having the operator mount the sample rack L inserted with the sample container T of the calibrator and the sample container T of the sample for reproducibility check, which is a normal sample, on the pre-analysis rack holder 41 and input the start instruction of the automatic calibration operation.

<Manual Calibration Operation>

The manual calibration operation in which the operator or the service man manually performs the calibration of the first measurement unit 2 and the second measurement unit 3 will be described. The operator or the service man pushes the sample setting portion open/close button 27 of the first measurement unit 2, and moves the sample container setting portion 25b to the priority sample setting position. Thereafter, the operator or the service man inserts the sample container T accommodating the sample for reproducibility check, which is a normal sample, to the sample container setting portion 25b, pushes the priority sample measurement start button 28, and starts the measurement of the sample for reproducibility check. The measurement of the sample for reproducibility check by the first measurement unit 2 is performed five times.

The operator or the service man determines whether or not variation in the five analysis results by the first measurement unit 2 of the sample for reproducibility check obtained in such manner is within a predetermined range, and checks the reproducibility of the analysis result of the first measurement unit 2. The reproducibility of the analysis result of the first measurement unit 2 may be automatically performed by the information processing unit 5, similar to the automatic calibration operation described above.

After the reproducibility check of the analysis result of the first measurement unit 2 is completed, the operator or the service man inserts the sample container T accommodating the calibrator to the sample container setting portion 25b, pushes the priority sample measurement start button 28, and starts the measurement of the sample for reproducibility check. The measurement of the calibrator by the first measurement unit 2 is performed five times. The operator or the service man also inputs the reference concentration of the calibrator to the information processing unit 5. Similar to the automatic calibration operation, the information processing unit 5 updates the first correction data D1 to calibrate the first measurement unit 2.

The operator or the service man then pushes the sample setting portion open/close button 37 of the second measurement unit 3 to move the sample container setting portion 35b to the priority sample setting position. Thereafter, the operator or the service man inserts the sample container T accommodating the sample for reproducibility check, which is a normal sample, to the sample container setting portion 25b, pushes the priority sample measurement start button 28, and starts the measurement of the sample for reproducibility check. This sample for reproducibility check may be the same sample as or a different sample from the sample for reproducibility check used in the reproducibility check of the first measurements unit 2. The measurement of the sample for reproducibility check by the second measurement unit 3 is performed five times.

The operator or the service man determines whether or not variation in the five analysis results by the second measurement unit 3 of the sample for reproducibility check obtained in such manner is within a predetermined range, and checks the reproducibility of the analysis result of the second measurement unit 3.

After the reproducibility check of the analysis result of the second measurement unit 3 is completed, the operator or the service man pushes the sample setting portion open/close button 27 of the first measurement unit 2 to move the sample container setting portion 25b to the priority sample setting position. Thereafter, the operator or the service man inserts the sample container T accommodating the sample for reproducibility check used in the reproducibility check of the analysis result of the second measurement unit 2 to the sample container setting portion 25b, pushes the priority sample measurement start button 28, and starts the measurement of the sample for reproducibility check. The measurement of the sample for reproducibility check by the first measurement unit 2 is performed once.

Figure 18:
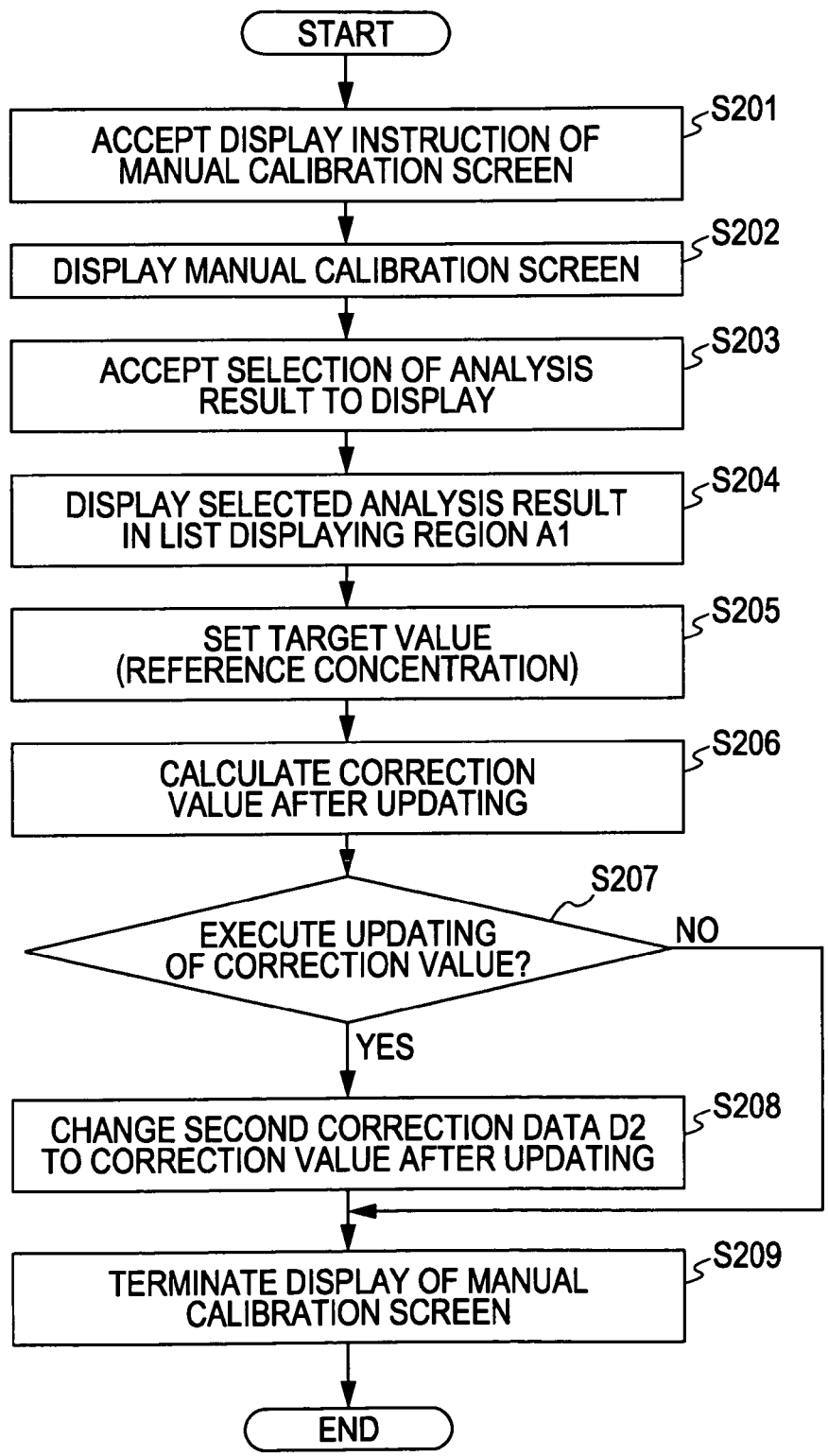
FIG. 18 is a flowchart showing a procedure of the manual calibration process of the second measurement unit by the CPU of the information processing unit.

After performing each measurement above, the operator or the service man performs manual calibration of the second measurement unit 3. FIG. 18 is a flowchart showing a procedure of the manual calibration process of the second measurement unit 3 by the CPU 51a.

First, the operator or the service man operates the input unit 53 to provide a display instruction of a manual calibration screen to the information processing unit 5. When an event of accepting the display instruction of the manual calibration screen occurs (step S201), the CPU 51a of the information processing unit 5 displays the manual calibration screen on the image display unit 52 (step S202).

FIG. 19 is a view showing one example of the manual calibration screen. The manual calibration screen W includes a list displaying region A1 displaying a list of a plurality of selected analysis results, an average value displaying region A2 displaying an average value of the plurality of analysis results for every item, a target value displaying region A3 displaying a target value (reference concentration) for every item, a before-updated correction value displaying region A4 displaying the correction value before updating for every item, and an after-updated correction value displaying region A5 displaying the correction value after updating for every item. The manual calibration screen also includes a target value setting button B1 for setting the target value, an OK button B2 for confirming the updated correction value, and a cancel button B3 for discarding the updated correction value so as not to update the correction value.

The list displaying region A1 displays the measurement date, the measurement time, the measurement unit used in the measurement, and the measurement value for each measurement item. The list displaying region A1 includes ten rows for displaying the analysis result to display ten analysis results. Buttons B4, B4, . . . for calling out a dialogue (not shown) to search for the analysis result are provided next to the display row of each analysis result, so that the operator or the service man can display the dialogue by operating the input unit 53 and selecting the button B4. The operator or the service man can search for the analysis result using such dialogue. For instance, a list of analysis results are displayed by inputting the sample ID, the measurement date and time, the measurement unit, and the like as the search key. The operator or the service man operates the input unit 53 to select the desired analysis result from the list, wherein when the CPU 51a accepts the selection of such analysis result (step S203), the CPU 51a displays the selected analysis result on the list displaying region A1 (step S204). In this case, the operator or the service man selects the analysis result of recent measurement date and time of a plurality of analysis results obtained by measuring the same sample with the same measurement unit. In the present embodiment, five analysis results of the sample for reproducibility check by the second measurement unit 3 are assumed to be selected.

As shown in FIG. 19, when five analysis results are selected, the measurement date and the measurement time of the analysis results, the device ID of the measurement unit (i.e., device ID of second measurement unit 3) used in the measurement, the analysis result of each item of the WBC, the RBC, the HGB, the PLT, and the like are displayed on the list displaying region A1. The average value of the analysis result of each item of the WBC, the RBC, the HGB, the PLT, and the like are displayed in the average value displaying region A2, and the correction value of the current second measurement unit 3 is displayed for every item in the before-updated correction value displaying region A4.

The operator or the service man operates the input unit 53 to select the target value setting button B1 in such state. A dialog (not shown) for target value setting is thereby displayed. In this dialogue, the analysis result to be used as a target value can be searched, or the target value can be directly input. The operator or the service man uses the relevant dialogue to select the analysis result of the sample for reproducibility check by the first measurement unit 2 after the calibration, and sets the same as the target value (step S205). When the CPU 51a accepts such operation, the CPU 51a displays the analysis result of the sample for reproducibility check by the first measurement unit 2 for every item on the target value displaying region A3. The correction value after updating is then automatically calculated by the CPU 51a (step S206), and the correction value after updating is displayed for every item on the after-updated correction value displaying region A5.

The operator or the service man operates the input unit 53 and selects the OK button B2 when using the correction value after updating that is being displayed. When the update instruction of the relevant correction value is provided to the CPU 51a (YES in step S207), the CPU 51a changes the second correction data D2 stored in the hard disc 51d to the correction value after updating (step S208), terminates the display of the manual calibration screen W (step S209), and terminates the process. The calibration of the second measurement unit 3 is thereby completed. The operator or the service man operates the input unit 53 to select the cancel button B3 when not using the correction value after updating that is being displayed. When accepting the instruction to cancel the updating of the relevant correction value (NO in step S207), the CPU 51a advances the process to step S209 and terminates the display of the manual calibration screen W without updating the second correction data D2 stored in the hard disc 51d, and terminates the process. The calibration of the second measurement unit 3 is thus not performed.

<Sample Measurement Operation>

The measurement operation of the sample by the sample analyzer 1 calibrated in the above manner will be described below. The measurement operation by the first measurement unit 2 will be described herein, but the measurement operation using the second measurement unit 3 is a similar operation. The operator mounts the sample rack L holding a plurality of sample containers T accommodating the sample on the pre-analysis rack holder 41. The operator operates the input unit 53 in this state to instruct the information processing unit 5 to execute the sample measurement operation. After accepting the instruction to execute the sample measurement operation, the information processing unit 5 controls the sample conveyance unit 4 when detecting the sample rack L mounted on the pre-analysis rack holder 41 with a sensor (not shown) to move the sample rack L with the pre-analysis rack holder 41, and thereafter, conveys the sample rack L on the rack conveyance portion 43 to convey the sample container T held in the sample rack L to the first sample supply position 43a.

Figure 20:
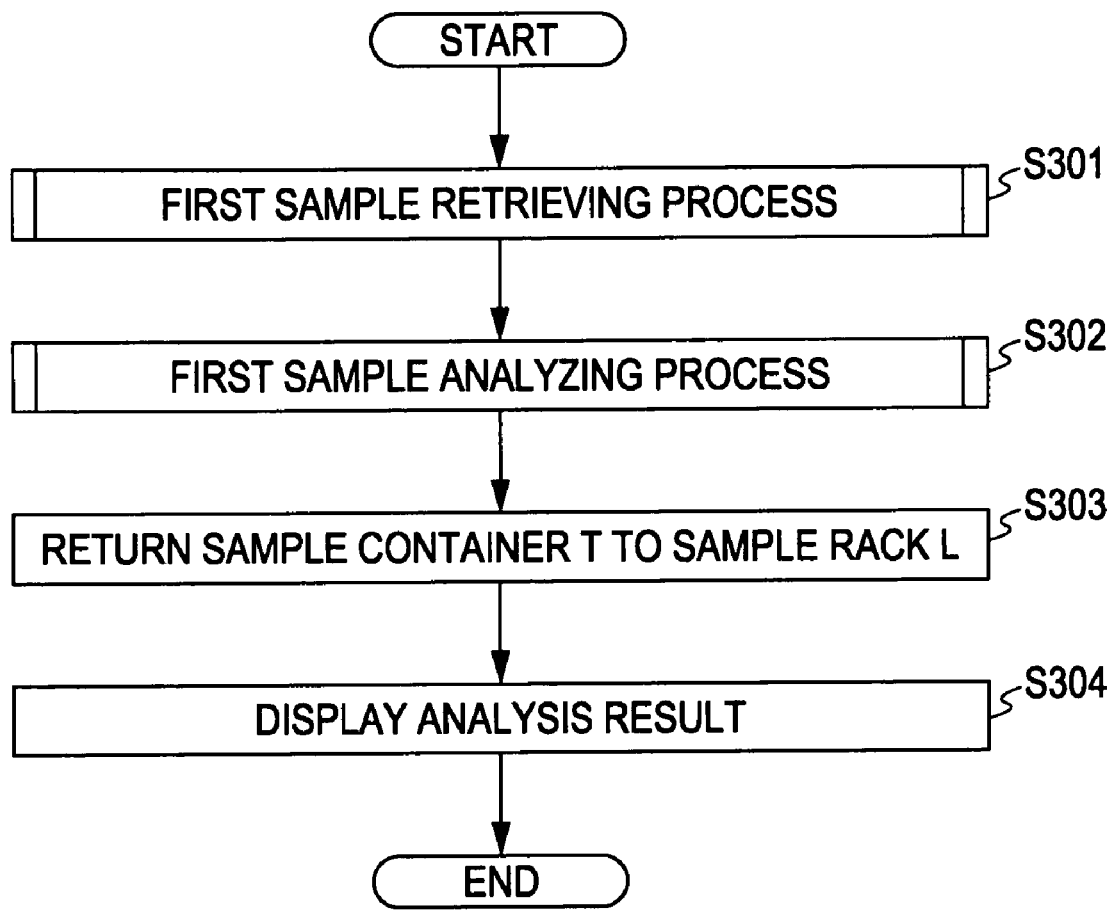
FIG. 20 is a flowchart showing a flow of the sample measurement operation of measuring the sample conveyed to the first sample supply position.

FIG. 20 is a flowchart showing a flow of the sample measurement operation for measuring the sample conveyed to the first sample supply position 43a. The CPU 51a executes the first sample retrieving process of retrieving the sample into the first measurement unit 2 from the sample container T at the first sample supply position 43a (step S301). The first sample retrieving process S301 is similar to the first sample retrieving process S52 shown in FIG. 13, and thus the description thereof will be omitted.

After the first sample retrieving process S301 is terminated, the CPU 51a executes the first sample analyzing process of measuring the sample by the first measurement unit 2 (step S302). In the first sample analyzing process S302, the analysis result is corrected by the first correction data D1 updated by the calibration. The first sample analyzing process S302 is similar to the first sample analyzing process S54 shown in FIG. 14, and thus the description thereof will be omitted.

After the first sample analyzing process S302 is terminated, the CPU 51a controls the sample container conveyance portion 25 to return the sample container T accommodating the sample back to the sample rack L (step S303), displays the analysis result obtained by the first sample analyzing process S302 on the image display device 52 (step S304), and terminates the process. In the analysis result displaying process S304, the analysis result screen including the analysis result corrected by the first correction data D1 after updating is displayed on the image display unit 52.

Thereafter, the sample rack L is pitch fed on the rack conveyance portion 43, and the sample container T is sequentially conveyed to the first sample supply position 43a. The sample container T positioned at the first sample supply position 43a is retrieved into the first measurement unit 2 and subjected to analysis, as described above. Such operation is repeated until the measurement of all samples is terminated. The sample analyzing operation is thereby terminated.

Generally, when calibrating the sample analyzer, an arbitrary sample is measured continuously for a plurality of times with the measurement unit, and a reproducibility check of the analysis result for checking whether or not the variation in the analysis result is within a predetermined range based on the respective measurement result is executed prior to the calibration. Therefore, according to the above configuration, the calibration of the second measurement unit 3 is performed using the analysis result of the sample for reproducibility check by the second measurement unit 3 of before the calibration, and thus the calibration of the second measurement unit can be performed by simply performing the measurement of the sample for reproducibility check with the first measurement unit 2. An expensive calibrator does not need to be used for the calibration of the second measurement unit 3, and the sample irrelevant to the calibration does not need to be measured in each of the first measurement unit 2 and the second measurement unit 3. Thus, the waste of the sample, the measurement time, and the reagent can be reduced.

As the calibrator and the sample for reproducibility check are automatically conveyed by the sample conveyance unit 4, and the reproducibility check of the analysis result and the calibration of the first measurement unit 2 as well as the reproducibility check of the analysis result and the calibration of the second measurement unit 3 are automatically performed, the work load of the operator or the service man in the reproducibility check and the calibration task of the sample analyzer 1 can be alleviated.

Furthermore, since manual calibration operation can be carried out, the operator or the service man can select the analysis result of the past (one or a few days before) on the manual calibration screen W, so that the sample does not need to be newly measured for the calibration of the second measurement unit 3. The waste of the sample, the measurement time, and the reagent can be thereby reduced.

Other Embodiments

In the embodiment described above, a configuration of measuring the sample for reproducibility check by the first measurement unit 2 after the calibration of the first measurement unit 2, and using the analysis result obtained as a result in the calibration of the second measurement unit 3 has been described, but this is not the sole case. The sample for reproducibility check used in the reproducibility check of the analysis result of the first measurement unit 2 may be measured over plural times before the calibration of the first measurement unit 2, the analysis result of before the correction obtained at the time may be averaged, the average value may be corrected by a correction value (i.e., first correction data D1 of after updating) of after the calibration of the first measurement unit 2, and the calibration of the second measurement unit 3 may be performed using the analysis result of after the correction and the analysis result obtained when the same sample for reproducibility check is measured with the second measurement unit 3. The sample for reproducibility check thus does not need to be measured by the first measurement unit 2 after the calibration of the first measurement unit 2.

In the embodiment described above, a configuration of measuring the sample for reproducibility check by the first measurement unit 2 after the calibration of the first measurement unit 2 and then measuring the sample for reproducibility check over plural times by the second measurement unit 3 in the automatic calibration operation has been described, but this is not the sole case. The sample for reproducibility check may be measured over plural times by the second measurement unit 3 after the calibration of the first measurement unit 2, and then the sample for reproducibility check may be measured by the first measurement unit 2 for calibration.

In the embodiment described above, the number of measurements of the sample for reproducibility check in the reproducibility check of the analysis result and the number of measurements of the calibrator in the calibration operation of the first measurement unit 2 are five times, but this is not the sole case. The number of measurements may be any number of measurements as long as it is plural times such as three times, seven times, or ten times. The number of measurements of the calibrator may be one. Furthermore, the number of measurements of the sample for reproducibility check and the number of measurements of the calibrator may be different.

In the embodiment described above, a configuration of executing all processes of the computer program 54a with a single computer 5a has been described, but this is not the sole case, and a distributed system of distributing the processes similar to the computer program 54a to a plurality of devices (computers) and executing the same may be adopted.

According to the sample analyzer of each embodiment described above, the cost required for the calibration of the sample analyzer can be reduced and the sample to use for the calibration can be reduced compared to the related art.

What is claimed is:

1. A sample analyzer comprising:
    a first measurement unit for measuring a sample;
    a second measurement unit for measuring a sample; and
    an information processing unit for acquiring a first analysis result based on a result of the measurement by the first measurement unit and a second analysis result based on a result of the measurement by the second measurement unit, wherein the information processing unit is configured to:
    correct the first analysis result based on a first correction value,
    correct the second analysis result based on a second correction value,
    update the first correction value based on an analysis result obtained through a measurement of a sample for calibration by the first measurement unit, and
    update the second correction value based on a plurality of analysis results obtained by measuring a first sample a plural times by the second measurement unit, and a corrected analysis result,
    wherein the corrected analysis result is obtained by correcting an analysis result obtained by measuring the first sample by the first measurement unit by using the first correction value updated by the information processing unit.

2. The sample analyzer of claim 1, wherein the information processing unit is further configured to determine whether or not variation in the plurality of analysis results obtained by measuring the first sample over a plurality of times by the second measurement unit is within a predetermined range.

3. The sample analyzer of claim 1, further comprising:
    a conveyance unit for conveying the first sample; and
    a conveyance controller for controlling the conveyance unit to convey the first sample to the first measurement unit and the second measurement unit; wherein
    the first measurement unit is configured to measure the first sample conveyed by the conveyance unit; and
    the second measurement unit is configured to measure the first sample conveyed by the conveyance unit over a plurality of times.

4. The sample analyzer of claim 3, wherein:
    the conveyance controller is configured to control the conveyance unit to convey the first sample to the first measurement unit, and convey the sample for calibration to the first sample measurement unit after the first sample is supplied to the first measurement unit;
    the first measurement unit is configured to measure the first sample conveyed by the conveyance unit over a plurality of times, and measures the sample for calibration conveyed by the conveyance unit; and
    the information processing unit is configured to determine whether or not variation in a plurality of analysis results obtained by measuring the first sample over a plurality of times by the first measurement unit is within a predetermined range.

5. The sample analyzer of claim 3, wherein the information processing unit comprises the conveyance controller.

6. The sample analyzer of claim 1, wherein:
    the information processing unit further comprises a memory for storing analysis result of the first sample;
    the information processing unit is configured to accept selection of a plurality of analysis results on the first sample by the second measurement unit from the plurality of analysis results stored in the memory; and
    the information processing unit is configured to update the second correction value based on the selected plurality of analysis results and the corrected analysis result of the first sample by the first measurement unit.

7. The sample analyzer of claim 1, wherein the information processing unit is configured to acquire an average value of an average of the plurality of analysis results obtained by measuring the first sample over a plurality of times by the second measurement unit, and to update the second correction value based on the corrected analysis result of the first sample by the first measurement unit and the average value of the plurality of analysis results by the second measurement unit.

8. The sample analyzer of claim 1, wherein the information processing unit is configured to output the second analysis result corrected by the second correction value.

9. The sample analyzer of claim 1, wherein the first sample is a sample for reproducibility check.

10. The sample analyzer of claim 1, wherein:
    the information processing unit comprises a first correction value memory for storing the first correction value; and
    the information processing unit updates the first correction value stored in the first correction value memory.

11. The sample analyzer of claim 1, wherein:
    the information processing unit comprises a second correction value memory for storing the second correction value; and
    the information processing unit updates the second correction value stored in the second correction value memory.

12. The sample analyzer of claim 1, wherein the first measurement unit has a configuration the same as the second measurement unit.

13. A calibration method of a sample analyzer comprising a first measurement unit and a second measurement unit; the method comprising steps of:
    first calibration step of updating a first correction value by using an analysis result obtained when the first sample measurement unit measures a sample for calibration, wherein the first correction value is to be used to correct a result of a measurement by the first measurement unit;
    first analyzing step of acquiring an analysis result based on a result of a measurement of a first sample by the first measurement unit;
    first correcting step of correcting the analysis result based on the updated first correction value;
    second analyzing step of acquiring a plurality of analysis results obtained by measuring the first sample over a plurality of times by the second sample measurement unit;
    second calibration step of updating a second correction value by using the plurality of analysis results obtained in the second analyzing step, and the corrected analysis result obtained in the first correcting step, wherein the second correction value is to be used to correct a result of a measurement by the second measurement unit.

14. The method of claim 13, further comprising second measurement unit reproducibility checking step of determining whether or not variation in the plurality of analysis results obtained by measuring the first sample over a plurality of times by the second sample measurement unit is within a predetermined range.

15. The method of claim 13, further comprising conveying step of conveying the first sample to the first measurement unit and the second measurement unit; wherein
    in the first analyzing step, the first sample conveyed by a conveyance unit is measured by the first measurement unit; and
    in the second analyzing step, the first sample conveyed by the conveyance unit is measured by the second measurement unit over a plurality of times.

16. The method of claim 13, further comprising:
    analysis result storing step of storing analysis result of a sample; and
    selecting step of selecting a plurality of analysis results on the first sample by the second measurement unit from the plurality of analysis results stored in the analysis result storing step; wherein
    in the second calibration step, the second correction value is updated based on the plurality of analysis results selected in the selecting step and the corrected analysis result of the first sample by the first measurement unit.

17. The method of claim 13, wherein in the second calibration step, an average value of an average of the plurality of analysis results obtained by measuring the first sample over a plurality of times by the second measurement unit is acquired, and the second correction value is updated based on the corrected analysis result of the first sample by the first measurement unit and the average value of the plurality of analysis results by the second measurement unit.

18. The method of claim 13, wherein the first sample is a sample for reproducibility check.

19. The method of claim 13, further comprising:
    first correction value storing step of storing the first correction value; and
    second correction value storing step of storing the second correction value; wherein
    in the first calibration step, the first correction value stored in the first correction value storing step is updated; and
    in the second calibration step, the second correction value stored in the second correction value storing step is updated.

20. A calibration method of a sample analyzer comprising a first measurement unit and a second measurement unit; the method comprising steps of:
    measuring a sample for calibration by the first measurement unit and calibrating the first measurement unit;
    measuring a sample for reproducibility check by the second measurement unit a plurality of times;
    determining whether or not variation in a plurality of analysis results obtained by measuring the sample for reproducibility check over a plurality of times is within a predetermined range;
    measuring the sample for reproducibility check by the calibrated first measurement unit and acquiring an analysis result of the sample for reproducibility check; and
    calibrating the second measurement unit based on the analysis result of the sample for reproducibility check by the first measurement unit and the plurality of analysis results of the sample for reproducibility check by the second measurement unit.

* * * * *